(12) United States Patent
Miyamoto et al.

(10) Patent No.: US 11,261,182 B2
(45) Date of Patent: Mar. 1, 2022

(54) CRYSTAL OF PYRIDO[3,4-D]PYRIMIDINE DERIVATIVE OR SOLVATE THEREOF

(71) Applicant: Teijin Pharma Limited, Tokyo (JP)

(72) Inventors: Hidetoshi Miyamoto, Tokyo (JP); Tsuyoshi Mizuno, Tokyo (JP); Gen Unoki, Tokyo (JP); Yuki Miyazawa, Tokyo (JP); Naoki Yajima, Tokyo (JP)

(73) Assignee: Teijin Pharma Limited, Tokyo (JP)

(*) Notice: Subject to any disclaimer, the term of this patent is extended or adjusted under 35 U.S.C. 154(b) by 343 days.

(21) Appl. No.: 16/463,501

(22) PCT Filed: Nov. 27, 2017

(86) PCT No.: PCT/JP2017/042437
§ 371 (c)(1),
(2) Date: May 23, 2019

(87) PCT Pub. No.: WO2018/097295
PCT Pub. Date: May 31, 2018

(65) Prior Publication Data
US 2021/0276997 A1    Sep. 9, 2021

(30) Foreign Application Priority Data
Nov. 28, 2016   (JP) .............................. JP2016-229973

(51) Int. Cl.
*C07D 471/04* (2006.01)
(52) U.S. Cl.
CPC ........ *C07D 471/04* (2013.01); *C07B 2200/13* (2013.01)
(58) Field of Classification Search
CPC .................................................. C07D 471/04
USPC .................................................. 514/252.16
See application file for complete search history.

(56) References Cited

U.S. PATENT DOCUMENTS

| 2003/0149001 A1 | 8/2003 | Barvian et al. |
| 2010/0105653 A1 | 4/2010 | Besong et al. |
| 2016/0083379 A1 | 3/2016 | Boloor et al. |
| 2018/0161329 A1 | 6/2018 | Mizuno et al. |

FOREIGN PATENT DOCUMENTS

| WO | 03/062236 A1 | 7/2003 |
| WO | 2010/020675 A1 | 2/2010 |
| WO | 2014/037750 A1 | 3/2014 |
| WO | 2016/194831 A | 8/2016 |
| WO | 2016194831 | * 12/2016 |

OTHER PUBLICATIONS

Yoshinori Nonomura et al., "Direct Modulation of Rheumatoid Inflammatory Mediator Expression in Retinoblastoma Protein-Dependent and -Independent Pathways by Cyclin-Dependent Kinase 4/6", Arthritis & Rheumatism2, Jul. 2006, vol. 54, No. 7, pp. 2074-2083 (10 pages total).
Ken Taniguchi et al., "Induction of the p16INK4a senescence gene as a new therapeutic strategy for the treatment of rheumatoid arthritis", Nature Medicine, Jul. 1999, vol. 5, No. 7, pp. 760-767 (8 pages total).
Hitoshi Osuga et al., "Cyclin-dependent kinases as a therapeutic target for stroke", PNAS, Aug. 29, 2000, vol. 97, No. 18, pp. 10254-10259 (6 pages total).
Ichiro Inoshima et al., "Induction of CDK inhibitor p21 gene as a new therapeutic strategy against pulmonary fibrosis", American Journal Physiology Lung Cell and Molecular Physiology, Apr. 2004, vol. 286, pp. L727-L733 (7 pages total).
Soren M. Johnson et al., "Mitigation of hematologic radiation toxicity in mice through pharmacological quiescence induced by CDK4/6 inhibition", The Journal of Clinical Investigation, Jul. 2010, vol. 120, No. 7, pp. 2528-2536 (9 pages total).
Malini Guha, "Blockbuster dreams for Pfizer's CDK inhibitor", Nature Biotechnology, Mar. 2013, vol. 31, No. 3, p. 187 (1 page total).
Robert A. Weinberg, "Tumor Suppressor Genes", Science, Nov. 22, 1991, vol. 254, pp. 1138-1146(9 pages total).
Communication, dated Oct. 8, 2019, issued in corresponding Ecuadorian Application No. SENADI-2019-37197.
Communication, dated Feb. 20, 2020, issued by the Indian Intellectual Property Office in Application No. 201917019864.
Paolo Innocenti et al., "Expanding the scope of fused pyrimidines as kinase inhibitor scaffolds: synthesis and modification of pyrido [3,4-d] pyrimidines", Organic & Biomolecular Chemistry, Jan. 21, 2015, vol. 13, No. 3, pp. 893-904 (14 pages total).

* cited by examiner

*Primary Examiner* — Niloofar Rahmani
(74) *Attorney, Agent, or Firm* — Sughrue Mion, PLLC

(57) ABSTRACT

Provided is a crystal of a novel pyrido[3, 4-d]pyrimidine derivative having excellent CDK 4/6 inhibitory activity. A crystal of a compound represented by formula (I). In the formula, $R^1$ represents a hydrogen atom or a $C_{1-3}$ alkyl group; $R^2$ represents a hydrogen atom or an oxo group; L represents a single bond or a $C_{1-3}$ alkylene group; and X represents CH or N.

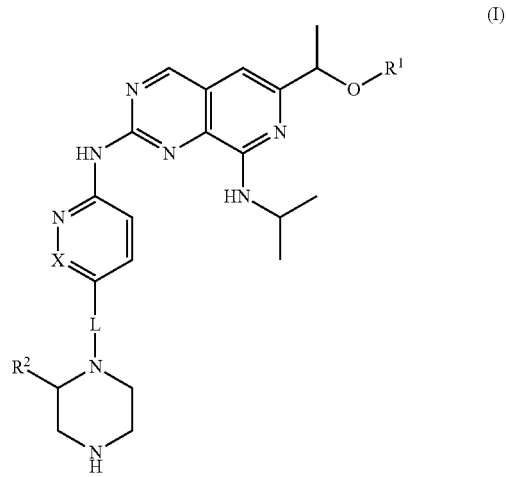

41 Claims, 28 Drawing Sheets

CRYSTAL OF PYRIDO[3,4-D]PYRIMIDINE DERIVATIVE OR SOLVATE THEREOF

CROSS REFERENCE TO RELATED APPLICATIONS

This application is a National Stage of International Application No. PCT/JP2017/042437 filed Nov. 27, 2017, claiming priority based on Japanese Patent Application No. 2016-229973 filed Nov. 28, 2016.

FIELD

The present invention relates to crystals of a pyrido[3,4-d]pyrimidine derivative or a solvate thereof that have inhibitory activity against cyclin-dependent kinase 4 and/or cyclin-dependent kinase 6 (hereinafter also referred to as "CDK4/6") and are useful for the prevention or treatment of rheumatoid arthritis, arteriosclerosis, pulmonary fibrosis, cerebral infarction and/or cancer.

BACKGROUND

CDK4/6 inhibitors can be used for treating various diseases caused by abnormal cell growth, including cancer, cardiovascular disorder, kidney disease, specific infections and autoimmune disease, and are expected to be effective in the treatment of rheumatoid arthritis, arteriosclerosis, pulmonary fibrosis, cerebral infarction, and cancer. The reasons why arresting the cell cycle and inhibiting the cell growth via CDK inhibition are expected to be effective in treating these conditions is based on the following technical finding.

Rheumatoid arthritis is known to involve the formation of pannus through hyperproliferation of synovial cells. It has been reported that this hyperproliferation can be reduced by the administration of a CDK4/6 inhibitor to the animal (NPL 1). A CDK4-cyclin D complex regulates the production of MMP3 in synovial cells derived from a patient with rheumatoid arthritis. The negative regulation of the activity of CDK4/6 inhibits not only the proliferation but also production of MMP3 (NPL 2).

Thus, CDK4/6 inhibitors are expected to exhibit both an inhibitory effect on proliferation of synovial cells and a cartilage protective effect in rheumatoid arthritis.

The induction of expression of the cell cycle inhibitory protein p21 with an adenoviral vector is effective in a murine pulmonary fibrosis model (NPL 3).

The level of cyclin D1/CDK4 is known to increase in a rat cerebral infarction model in association with neuronal death caused by local ischemia. The neuronal death is reduced by administering flavopiridol, which is a nonselective CDK inhibitor (NPL 4).

The cyclin D-CDK4/6-INK4a-Rb pathway is frequently detected in human cancer caused by abnormality of any factors contributing to growth of cancer cells, such as loss of functional p16INK4a, overexpression of cyclin D1, overexpression of CDK4, or loss of functional Rb (NPL 5). Such abnormality promotes the cell cycle progression from the G1 phase to the S phase, and this pathway certainly plays an important role in oncogenic transformation or abnormal growth of cancer cells.

CDK4/6 inhibitors may be effective, particularly for tumors involving abnormality in genes that activate the CDK4/6 kinase activity, such as cancers involving the translocation of cyclin D, cancers involving the amplification of cyclin D, cancers involving the amplification or overexpression of CDK4 or CDK6, and cancers involving the inactivation of p16. CDK4/6 inhibitors may be effective for the treatment of cancers involving genetic abnormality in the upstream regulator of cyclin D, the amount of which increases due to defects in the upstream regulator.

In fact, many compounds that inhibit the CDK4/6 activity have been synthesized and disclosed in the art, and such compounds have been clinically tested for the treatment of cancers, such as breast cancer (NPL 6).

Most acute and severe radiotherapeutic and chemotherapeutic toxicities are caused by the effects on stem cells and progenitor cells. A CDK4/6 inhibitor causes temporary cell cycle arrest to hematopoietic stem and progenitor cells, and protects them from radiotherapeutic or chemotherapeutic cytotoxicity. After the treatment with the inhibitor, hematopoietic stem and progenitor cells (HSPCs) return from the temporary dormancy and then function normally. Thus, the chemotherapeutic resistance with use of a CDK4/6 inhibitor is expected to provide a significant protection of bone marrow (NPL 7).

Hence, CDK4/6 inhibitors are expected to be effective for the treatment of, e.g., rheumatoid arthritis, arteriosclerosis, pulmonary fibrosis, cerebral infarction, or cancer, and the protection of bone marrow, in particular, for the treatment of rheumatoid arthritis or cancer and the protection of bone marrow.

Inhibitors of CDK including CDK4/6 are described in PTLs 1 and 2.

LIST OF CITATIONS

Patent Literature

[PTL1] WO2003/062236A
[PTL2] WO2010/020675A

Non-Patent Literature

[NPL 1] Taniguchi, K et al., Nature Medicine, Vol. 5, p. 760-767 (1999)
[NPL 2] Nonomura Y et al., Arthritis & Rheumatology 2006, July; 54 (7): p. 2074-83
[NPL 3] American Journal Physiology: Lung Cellular and Molecular Physiology, 2004, Vol. 286, p. L727-L733
[NPL 4] Proceedings of the National Academy of Sciences of the United States of America, 2000, Vol. 97, p. 10254-10259
[NPL 5] Science, Vol. 254, p. 1138-1146 (1991)
[NPL 6] Guha M, Nature Biotechnology 2013, March; 31 (3): p. 187
[NPL 7] Journal of Clinical Investigation 2010; 120 (7): p. 2528-2536

SUMMARY

Problem to be Solved by the Invention

An object of the present invention is to provide a novel crystal of a pyrido[3,4-d]pyrimidine derivative or a solvate thereof that exhibits excellent CDK4/6 inhibitory activity.

Means to Solve the Problem

Having conducted extensive studies for achieving the object above, the present inventors have found that pyrido[3,4-d]pyrimidine derivatives having specific structures exhibit excellent CDK4/6 inhibitory activity.

The present inventors have also found that some of these compounds can form crystals that are chemically stable and suitable as active pharmaceutical ingredients.

Thus, the present invention relates to a crystal of a compound represented by formula (I) or a solvate thereof.

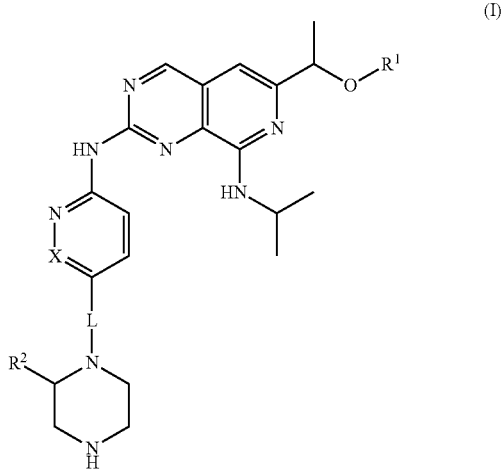

(I)

In the formula, $R^1$ represents a hydrogen atom or a $C_{1-3}$ alkyl group, $R^2$ represents a hydrogen atom or an oxo group (in the case of a oxo group, $R^2$ is bound to the piperazine ring via a double bond), L represents a single bond or a $C_{1-3}$ alkylene group, and X represents CH or N.

Effect of the Invention

The present invention provides a crystal of a pyrido[3,4-d]pyrimidine derivative or a solvate thereof that exhibits excellent CDK4/6 inhibitory activity and is useful as a prophylactic or therapeutic drug of, e.g., rheumatoid arthritis, arteriosclerosis, pulmonary fibrosis, cerebral infarction and/or cancer.

The crystal according to the present invention can be used as an active pharmaceutical ingredient in the manufacture of a pharmaceutical product.

BRIEF DESCRIPTION OF DRAWINGS

FIGS. 17-1 and 17-2 are solid NMR spectra ($^{13}C$) of Crystal D of 1-(6-((6-(((1R)-1-hydroxyethyl)-8-(isopropylamino)pyrido[3,4-d]pyrimidine-2-yl)amino)-3-pyridyl)piperazine-2-one. FIG. 17-1 is a spectrum obtained in the 6500 Hz mode, and FIG. 17-2 is a spectrum obtained in the 14000 Hz mode.

FIGS. 19-1 and 19-2 are solid NMR spectra ($^{13}C$) of Crystal A of 1-(6-((6-(((1R)-1-hydroxyethyl)-8-(isopropylamino)pyrido[3,4-d]pyrimidine-2-yl)amino)-3-pyridyl)piperazine-2-one. FIG. 19-1 is a spectrum obtained in the 6500 Hz mode, and FIG. 19-2 is a spectrum obtained in the 14000 Hz mode.

FIGS. 21-1 and 21-2 are solid NMR spectra ($^{13}C$) of Crystal A of 1-(6-((6-(((1R)-1-methoxyethyl)-8-(isopropylamino)pyrido[3,4-d]pyrimidine-2-yl)amino)-3-pyridazyl)piperazine. FIG. 21-1 is a spectrum obtained in the 6500 Hz mode, and FIG. 21-2 is a spectrum obtained in the 14000 Hz mode.

FIGS. 23-1 and 23-2 are solid NMR spectra ($^{13}$C) of Crystal A of (R)—N8-isopropyl-6-(1-methoxyethyl)-N2-(5-(piperazine-1-ylmethyl)pyridin-2-yl)pyrido[3,4-d]pyrimidine-2,8-diamine. FIG. 23-1 is a spectrum obtained in the 6500 Hz mode, and FIG. 23-2 is a spectrum obtained in the 14000 Hz mode.

MODES FOR CARRYING OUT THE INVENTION

The crystals according to the present invention are characterized by powder X-ray diffraction spectrometry (XRD), differential scanning calorimetry (DSC), Fourier transform infrared absorption spectrometry (hereinafter referred to as "infrared absorption spectrum") and/or solid NMR spectrometry. The powder X-ray diffraction (XRD) spectra of these crystals exhibit distinctive patterns, each of these crystals having specific values at a diffraction angle of 2θ. These crystals also exhibit distinctive thermal behaviors according to differential scanning calorimetry (DSC). The infrared absorption spectra of these crystals exhibit distinctive patterns, each of these crystals having a specific infrared absorption spectrum with a distinctive wave number. The $^{13}$C solid NMR spectra of these crystals exhibit distinctive patterns, each of these crystals having specific chemical shifts (ppm). The $^{15}$N solid NMR spectra of these crystals exhibit distinctive patterns, each of these crystals having specific chemical shifts (ppm).

While the present invention encompasses any crystal of a compound represented by formula (I), the following description will be focused on, as preferred embodiments thereof, nine crystals of the following three compounds:

1-(6-((6-((1R)-1-hydroxyethyl)-8-(isopropylamino)pyrido[3,4-d]pyrimidine-2-yl)amino)-3-pyridyl)piperazine-2-one (hereinafter also referred to as "Compound (a)");

1-(6-((6-((1R)-1-methoxyethyl)-8-(isopropylamino)pyrido[3,4-d]pyrimidine-2-yl)amino)-3-pyridazyl)piperazine- (hereinafter also referred to as "Compound (b)"); and (R)—N8-isopropyl-6-(1-methoxyethyl)-N2-(5-(piperazine-1-ylmethyl)pyridin-2-yl)pyrido[3,4-d]pyrimidine-2,8-diamine (hereinafter also referred to as "Compound (c)").

Figure 1:
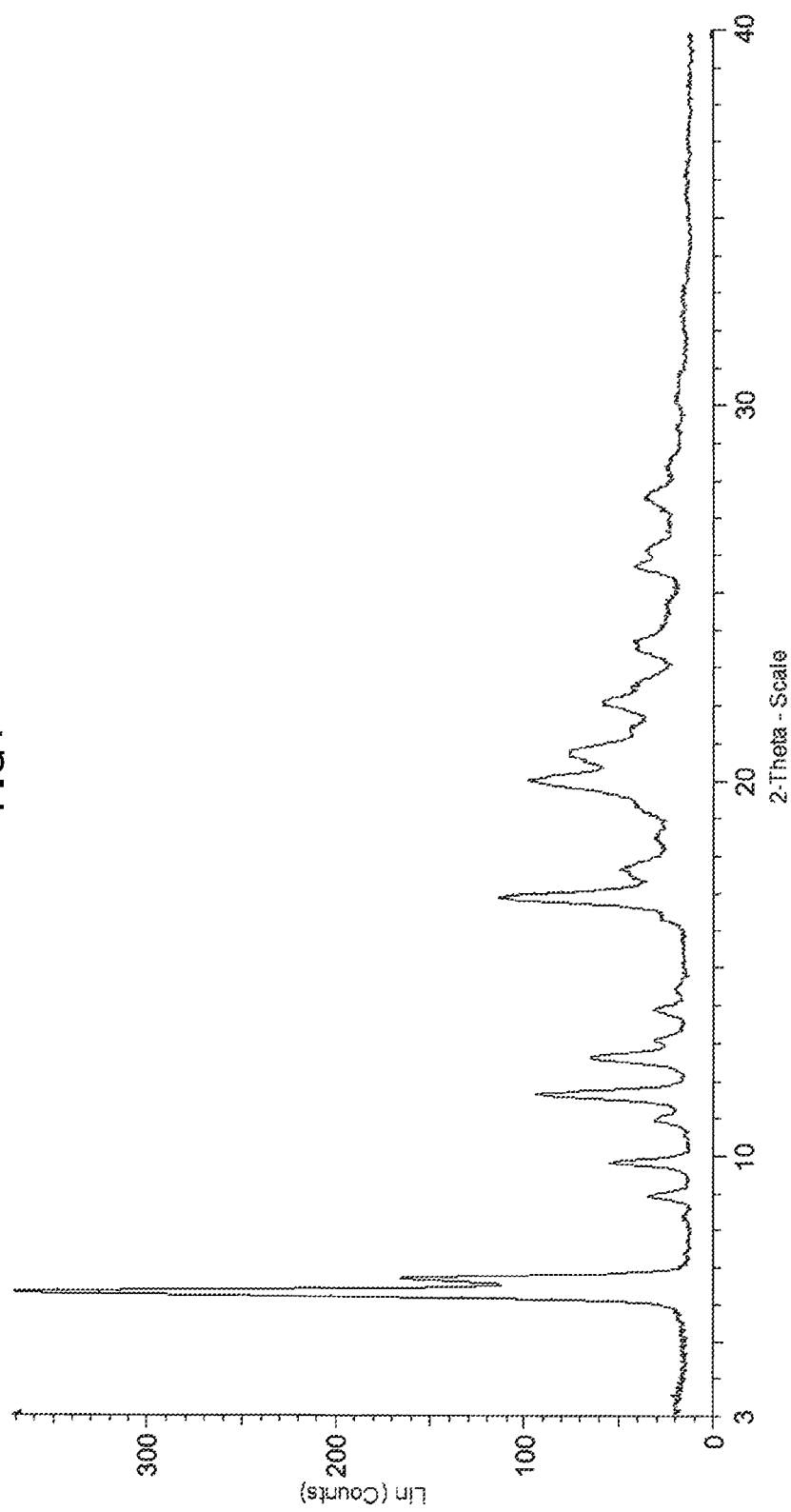
FIG. 1 is a powder X-ray diffraction spectrum of Crystal D of 1-(6-((6-(((1R)-1-hydroxyethyl)-8-(isopropylamino)pyrido[3,4-d]pyrimidine-2-yl)amino)-3-pyridyl)piperazine-2-one.

Crystal D of Compound (a) exhibits distinctive peaks at diffraction angles 2θ=6.3°, 6.6°, 11.6°, 16.9° and 20.0° on a powder X-ray diffraction spectrum. Crystal D of Compound (a) exhibits a pattern as shown in FIG. 1 on a powder X-ray diffraction spectrum.

Crystal D of Compound (a) exhibits an endothermic peak with an extrapolated onset temperature of 277° C. according to differential scanning calorimetry (DSC).

Figure 10:
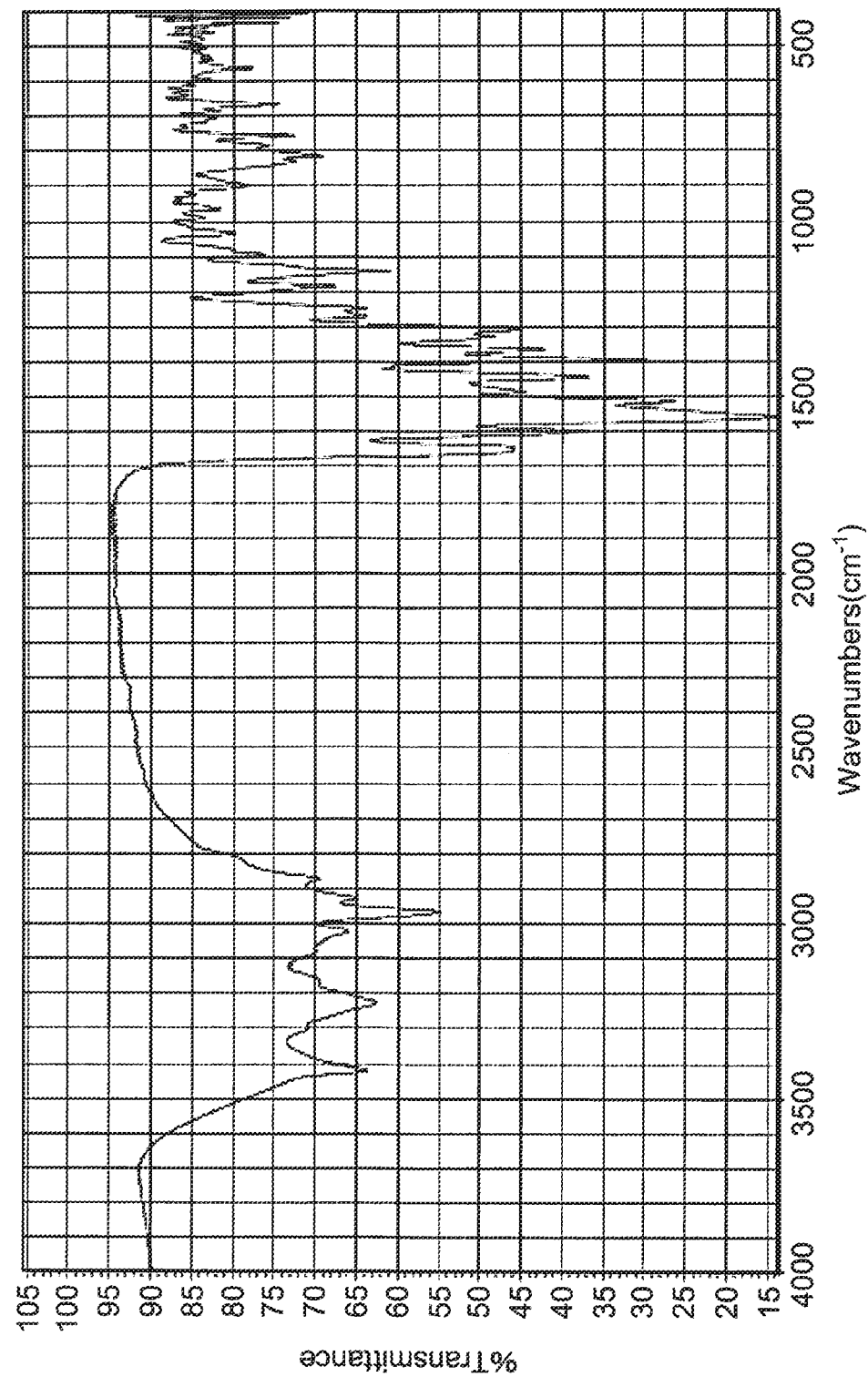
FIG. 10 is an infrared absorption spectrum of Crystal D of 1-(6-((6-(((1R)-1-hydroxyethyl)-8-(isopropylamino)pyrido[3,4-d]pyrimidine-2-yl)amino)-3-pyridyl)piperazine-2-one.

Crystal D of Compound (a) exhibits absorption peaks at wave numbers of 703 cm$^{-1}$, 896 cm$^{-1}$ and 3418 cm$^{-1}$ on a distinctive infrared absorption spectrum obtained according to the KBrtablet method. Crystal D of Compound (a) also exhibits an infrared absorption spectrum chart as shown in FIG. 10.

Figures 1, 17:
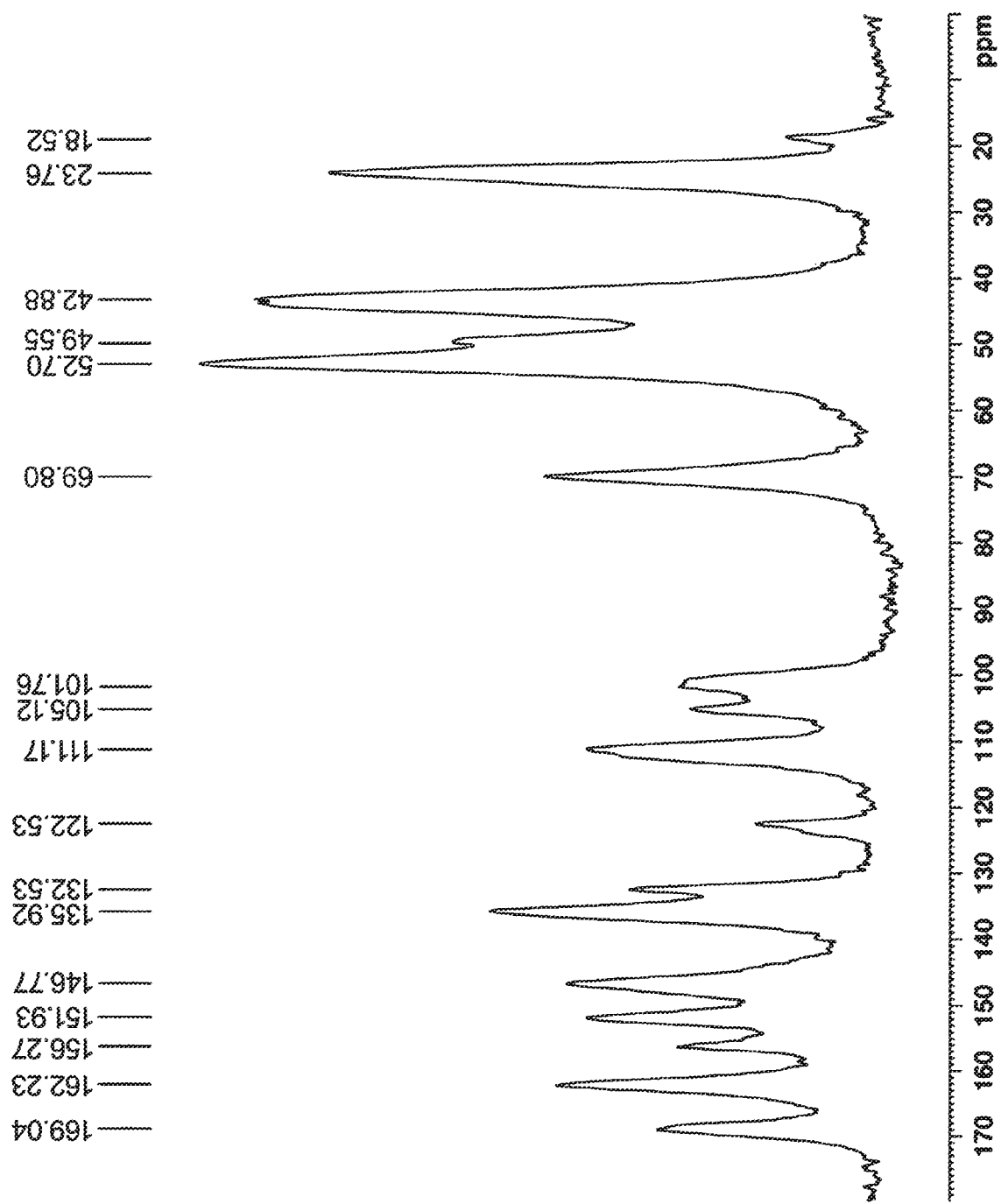
Figures 2, 17:
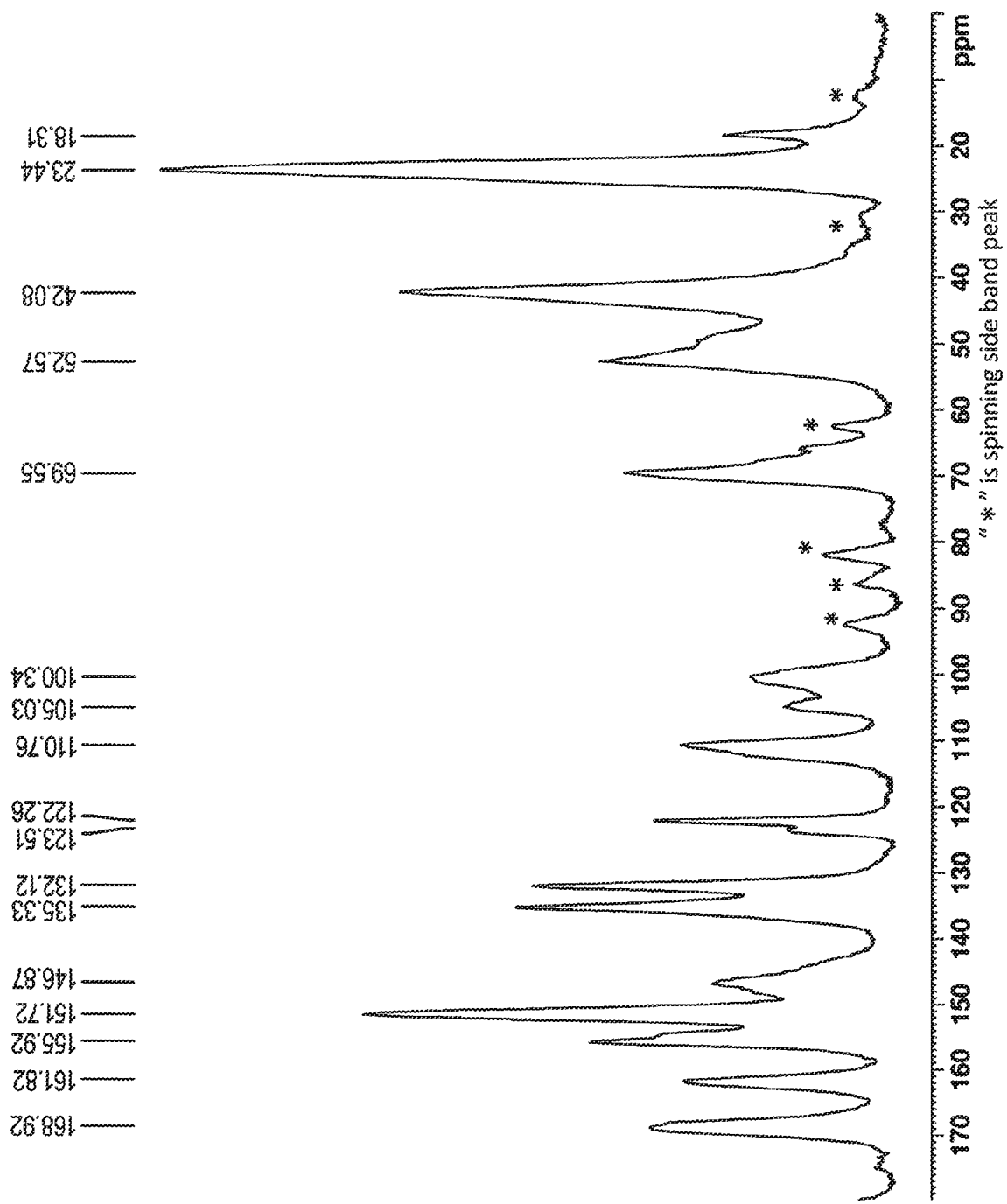

Crystal D of Compound (a) exhibits chemical shifts of 136.0 ppm, 111.2 ppm, 105.1 ppm, 101.8 ppm, 52.7 ppm, 49.6 ppm, 42.9 ppm, 23.8 ppm and 18.5 ppm on a $^{13}$C solid NMR spectrum. Crystal D of Compound (a) also exhibits a $^{13}$C solid NMR spectrum chart as shown in FIG. 17-1 (6500 Hz) and FIG. 17-2 (14000 Hz).

Figure 18:
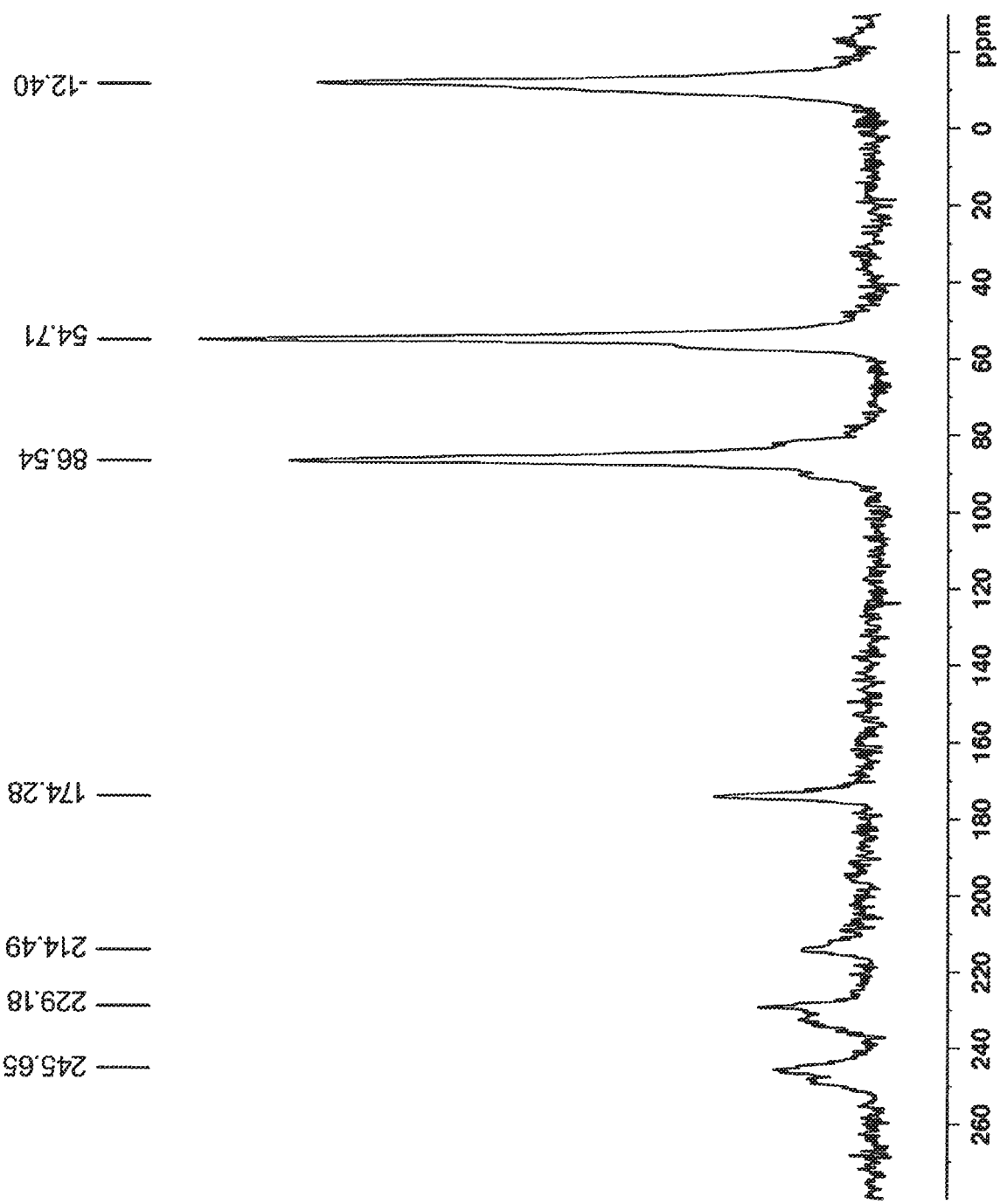
FIG. 18 is a solid NMR spectrum ($^{15}N$) of Crystal D of 1-(6-((6-(((1R)-1-hydroxyethyl)-8-(isopropylamino)pyrido[3,4-d]pyrimidine-2-yl)amino)-3-pyridyl)piperazine-2-one.

Crystal D of Compound (a) exhibits chemical shifts at 248.6 ppm, 245.7 ppm, 229.2 ppm, 214.5 ppm, 174.3 ppm, 86.5 ppm, 54.7 ppm and −12.4 ppm on a $^{15}$N solid NMR spectrum. Crystal D of Compound (a) also exhibits a $^{15}$N solid NMR spectrum chart as shown in FIG. 18.

Figure 2:
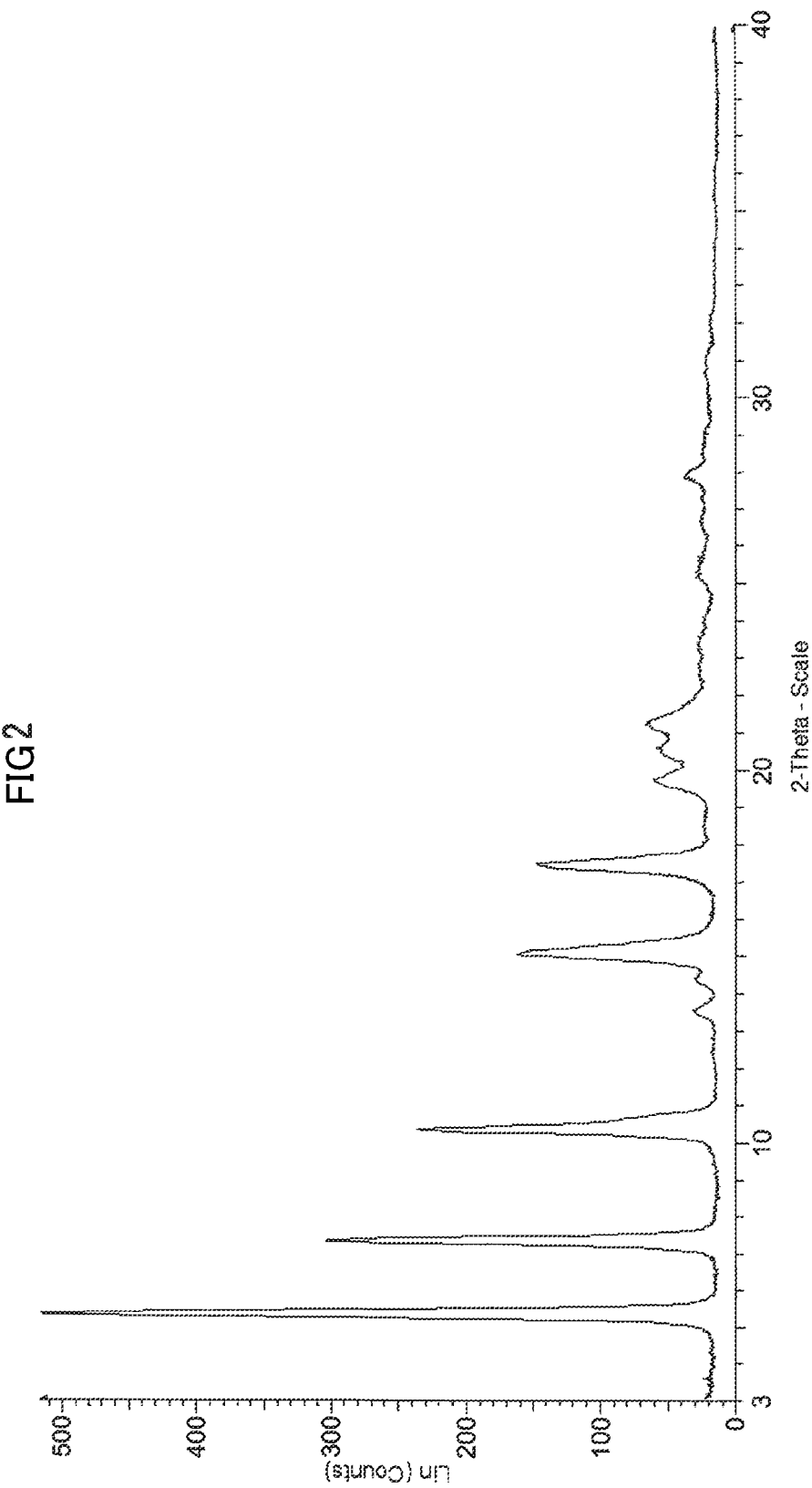
FIG. 2 is a powder X-ray diffraction spectrum of Crystal A of 1-(6-((6-(((1R)-1-hydroxyethyl)-8-(isopropylamino)pyrido[3,4-d]pyrimidine-2-yl)amino)-3-pyridyl)piperazine-2-one.

Crystal A of Compound (a) exhibits distinctive peaks at diffraction angles 2θ=5.3°, 7.3°, 10.3°, 15.1° and 17.4° on a powder X-ray diffraction spectrum. Crystal A of Compound (a) also exhibits a pattern as shown in FIG. 2 on a powder X-ray diffraction spectrum.

Crystal A of Compound (a) exhibits an endothermic peak with an extrapolated onset temperature of 277° C. according to differential scanning calorimetry (DSC).

Figure 11:
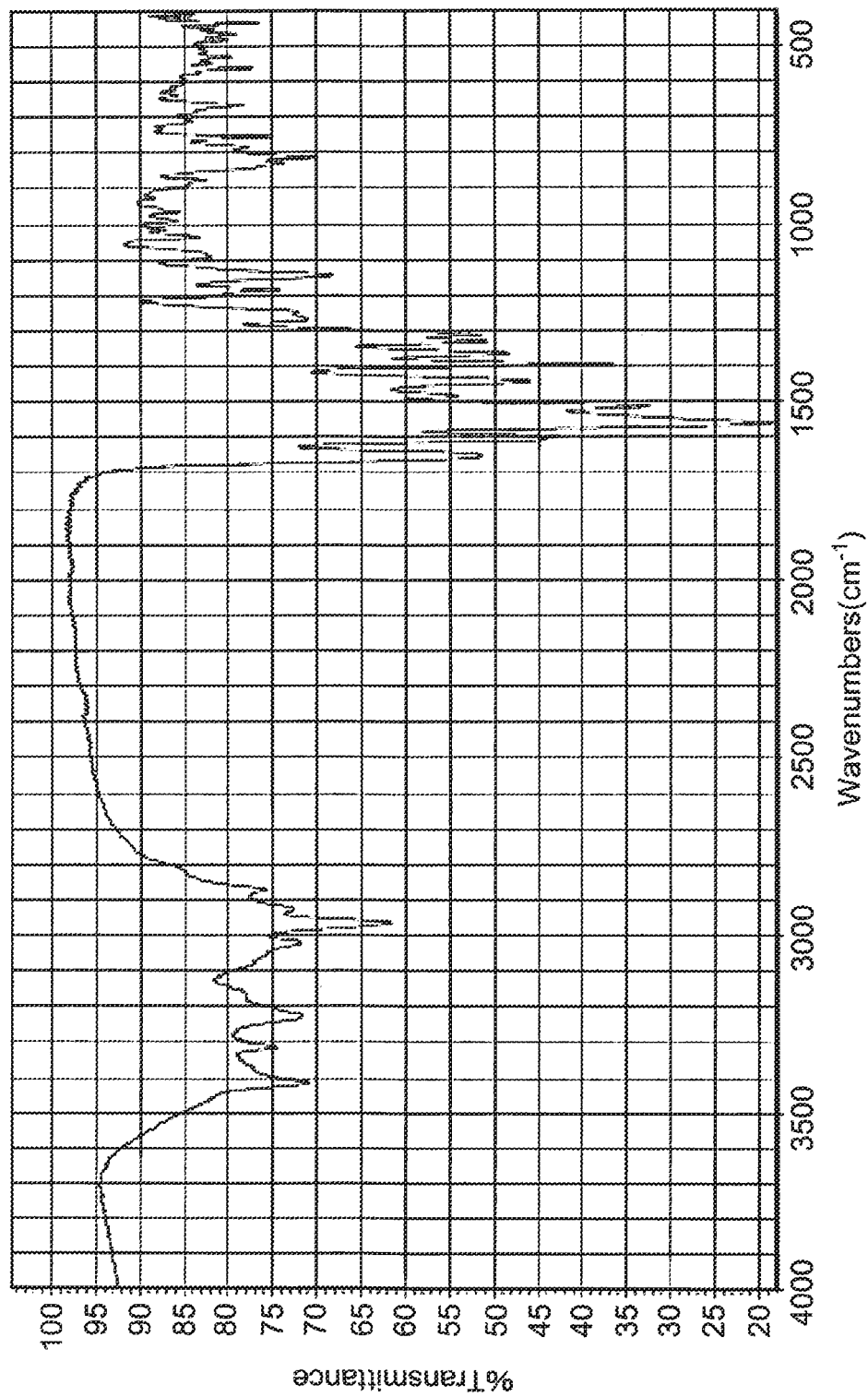
FIG. 11 is an infrared absorption spectrum of Crystal A of 1-(6-((6-(((1R)-1-hydroxyethyl)-8-(isopropylamino)pyrido[3,4-d]pyrimidine-2-yl)amino)-3-pyridyl)piperazine-2-one.

Crystal A of Compound (a) exhibits absorption peaks at wave numbers of 874 cm$^{-1}$, 1330 cm$^{-1}$ and 3314 cm$^{-1}$ on a distinctive infrared absorption spectrum obtained according to the KBrtablet method. Crystal A of Compound (a) also exhibits an infrared absorption spectrum chart as shown in FIG. 11.

Figures 1, 19:
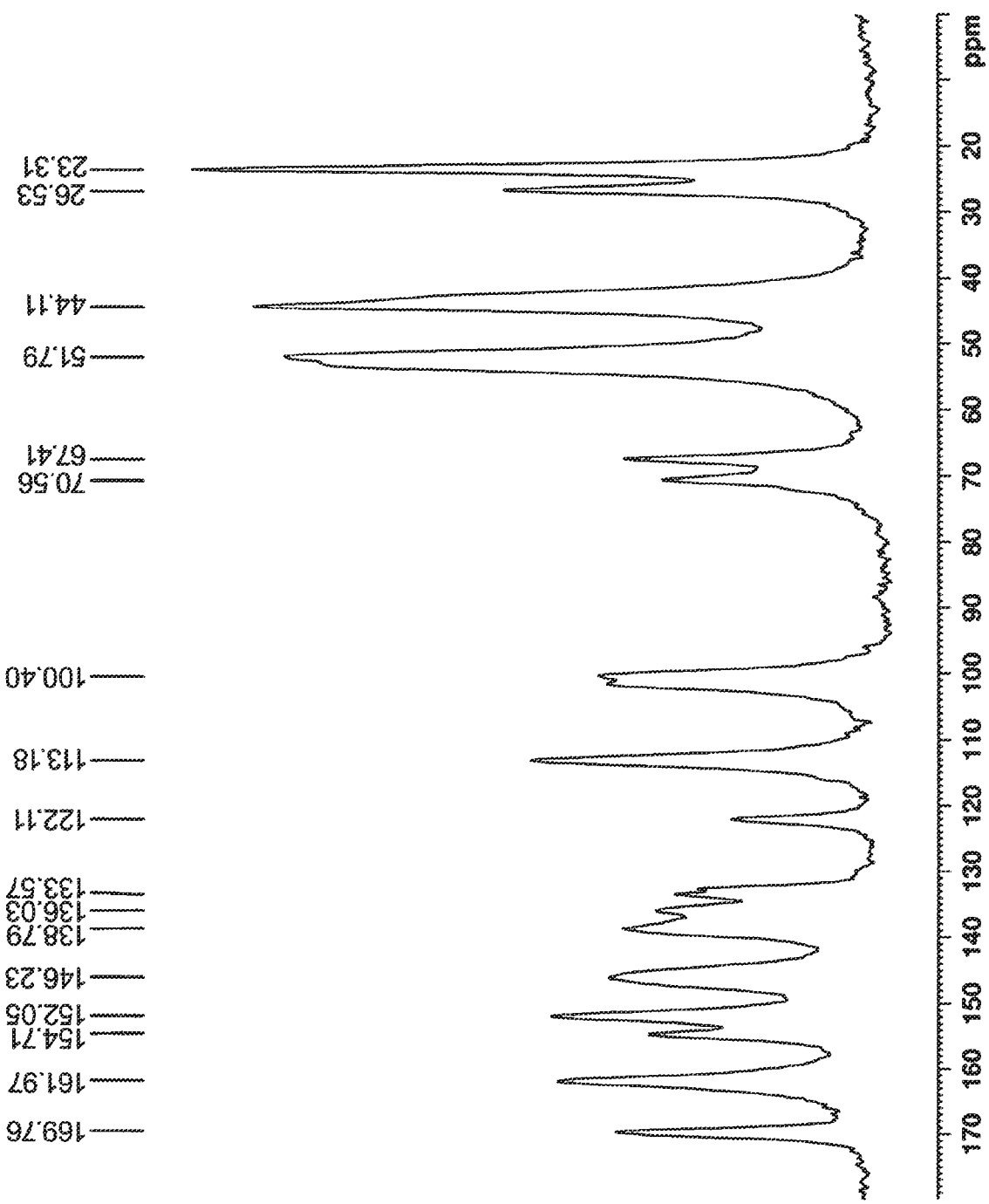
Figures 2, 19:
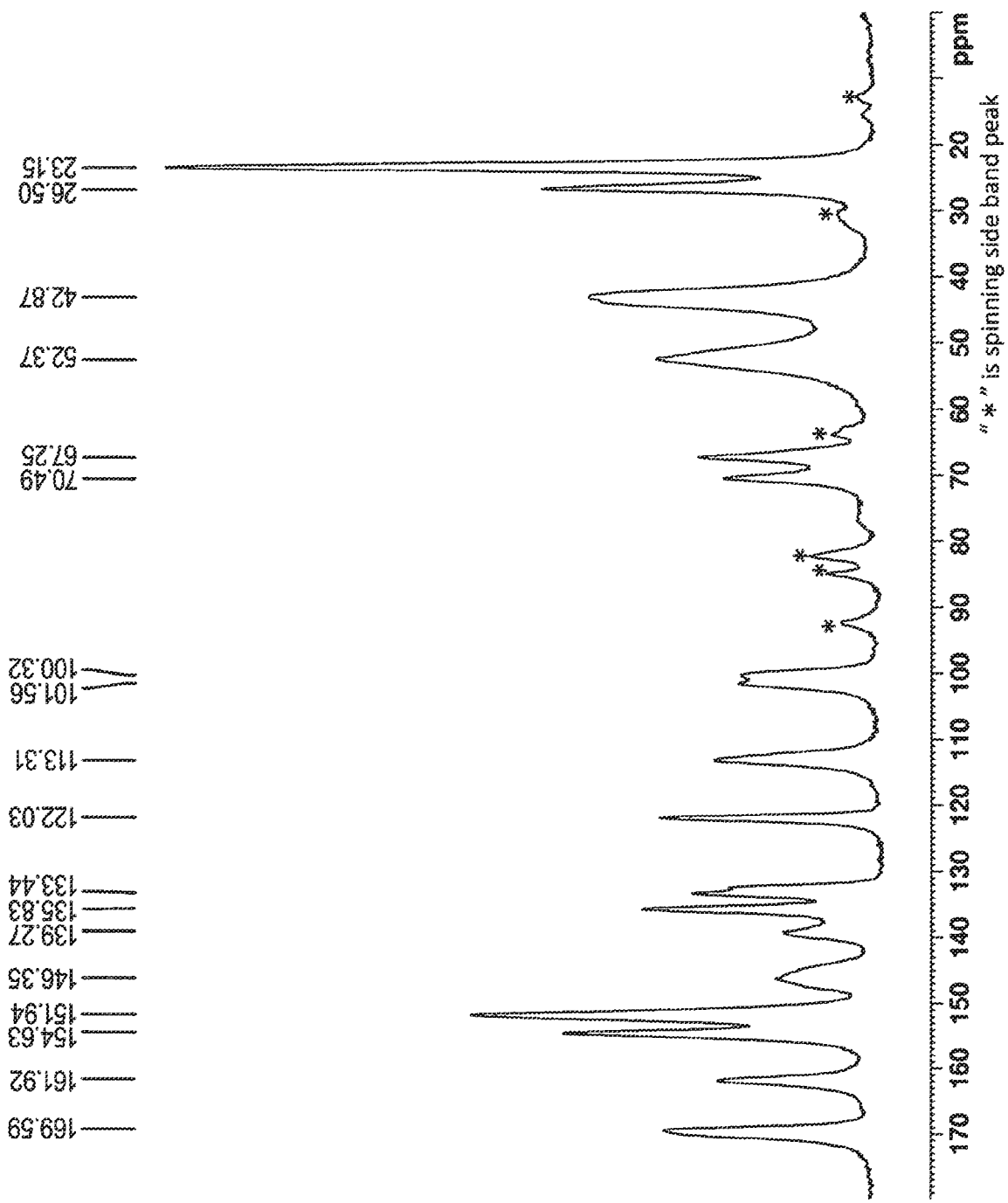

Crystal A of Compound (a) exhibits chemical shifts of 154.7 ppm, 138.8 ppm, 133.6 ppm, 113.2 pm, 101.6 ppm, 100.4 ppm, 67.4 ppm, 51.8 ppm, 26.6 ppm and 23.3 ppm on a $^{13}$C solid NMR spectrum. Crystal D of Compound (a) also exhibit a $^{13}$C solid NMR spectrum chart as shown in FIG. 19-1 (6500 Hz) and FIG. 19-2 (14000 Hz).

Figure 20:
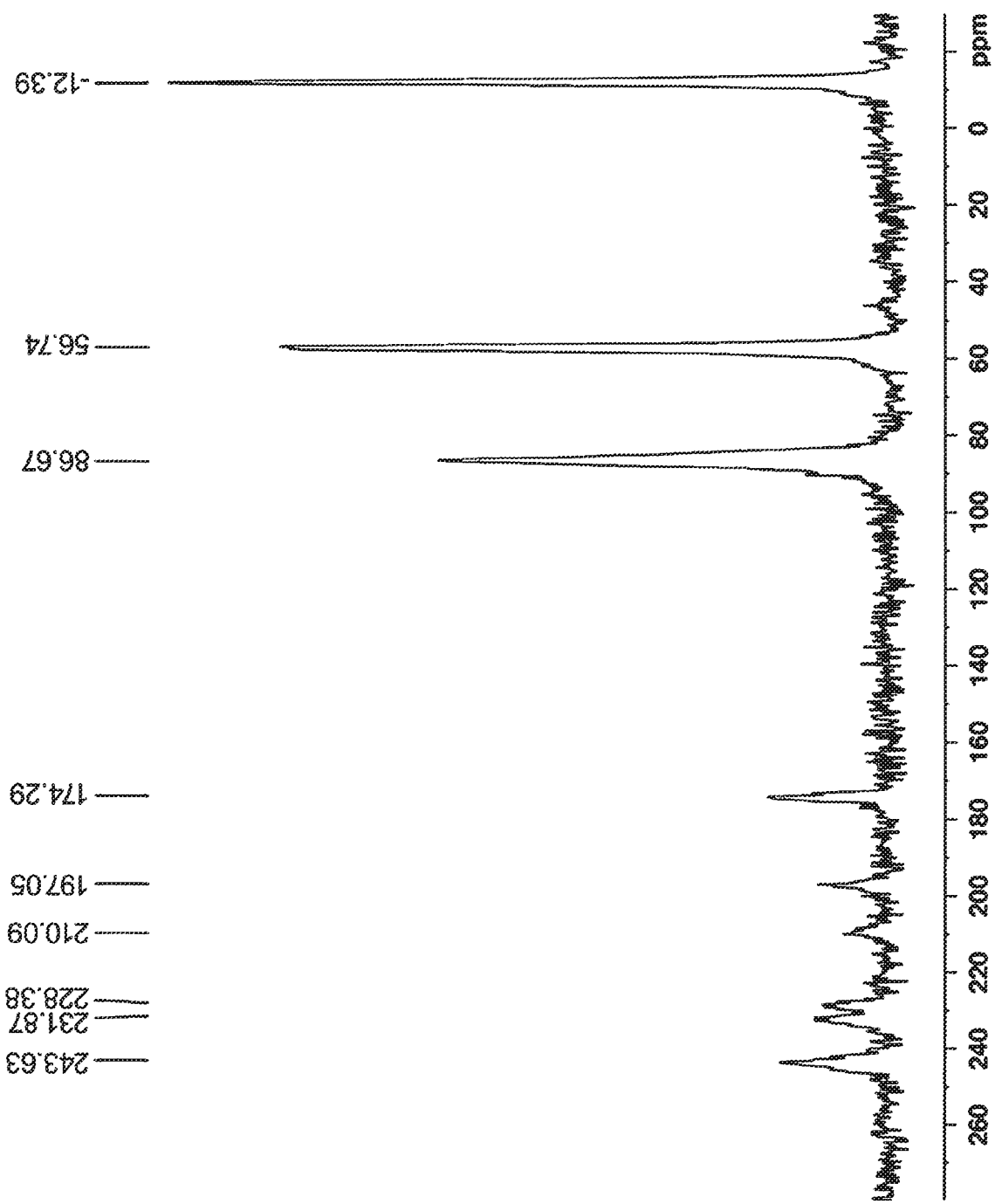
FIG. 20 is a solid NMR spectrum ($^{15}N$) of Crystal A of 1-(6-((6-(((1R)-1-hydroxyethyl)-8-(isopropylamino)pyrido[3,4-d]pyrimidine-2-yl)amino)-3-pyridyl)piperazine-2-one.

Crystal A of Compound (a) exhibits chemical shifts at 243.6 ppm, 86.7 ppm, 56.7 ppm and −12.4 ppm on a $^{15}$N solid NMR spectrum. Crystal A of Compound (a) also exhibits a $^{15}$N solid NMR spectrum chart as shown in FIG. 20.

Figure 6:
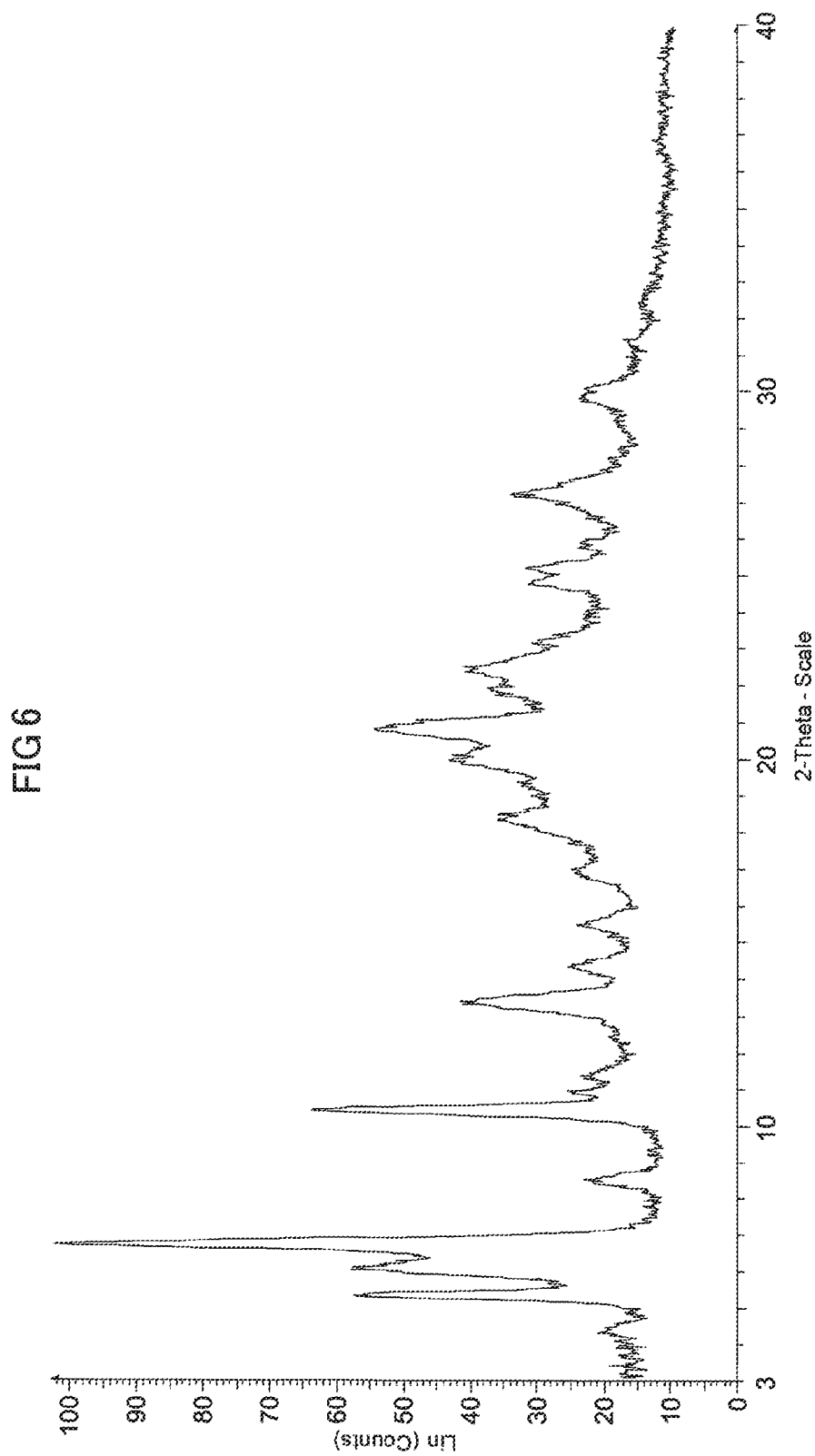
FIG. 6 is a powder X-ray diffraction spectrum of Crystal B of 1-(6-((6-(((1R)-1-hydroxyethyl)-8-(isopropylamino)pyrido[3,4-d]pyrimidine-2-yl)amino)-3-pyridyl)piperazine-2-one.

Crystal B of Compound (a) exhibits distinctive peaks at diffraction angles 2θ=5.3°, 6.0°, 6.7°, 10.4° and 20.8° on a powder X-ray diffraction spectrum. Crystal B of Compound (a) also exhibits a pattern as shown in FIG. 6 on a powder X-ray diffraction spectrum.

Crystal B of Compound (a) exhibits an endothermic peak with an extrapolated onset temperature of 271° C. according to differential scanning calorimetry (DSC).

Figure 7:
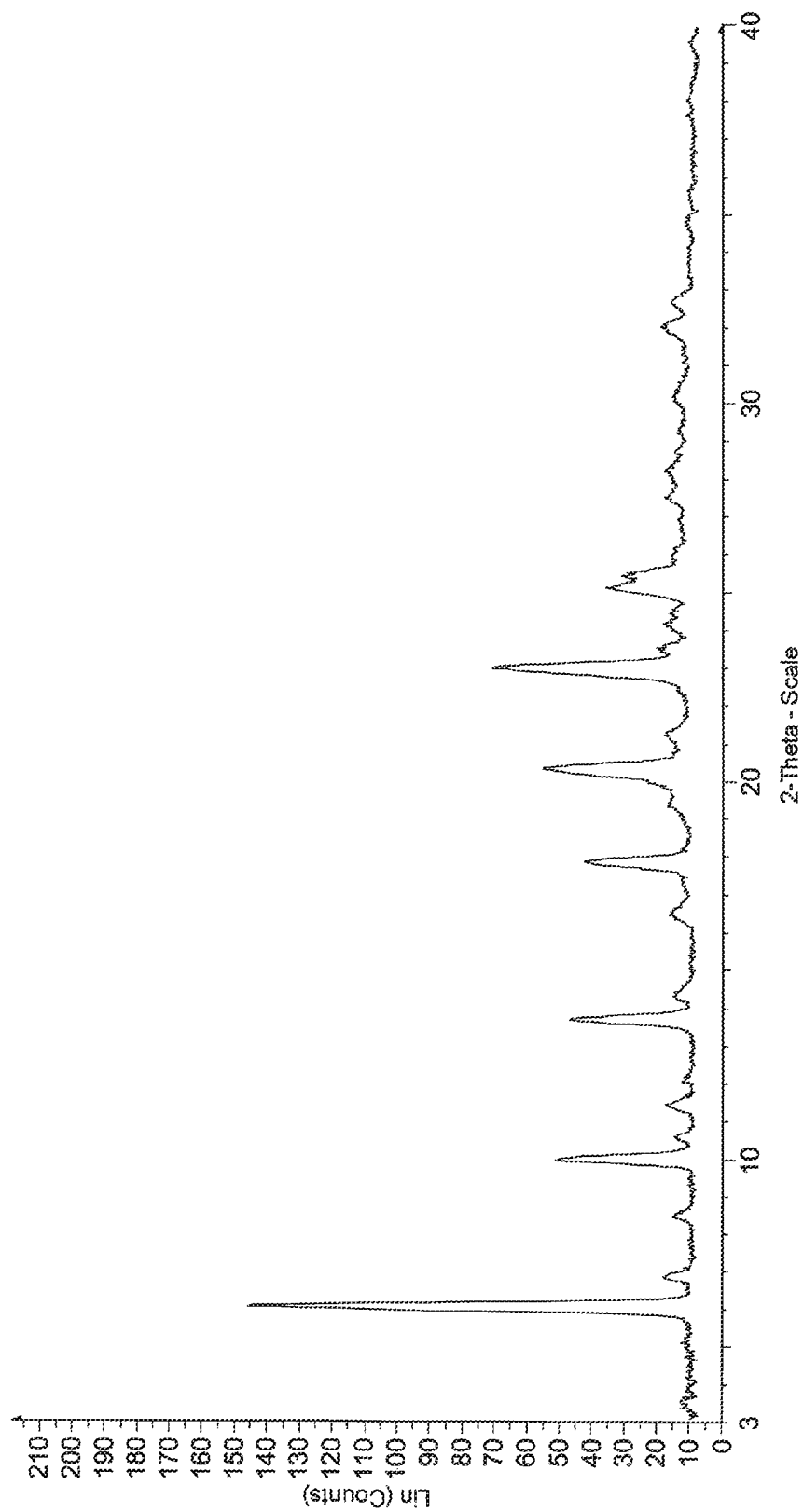
FIG. 7 is a powder X-ray diffraction spectrum of a crystal (Crystal C) of a solvate of 1-(6-((6-(((1R)-1-hydroxyethyl)-8-(isopropylamino)pyrido[3,4-d]pyrimidine-2-yl)amino)-3-pyridyl)piperazine-2-one with dimethyl sulfoxide.

Crystal C of Compound (a) exhibits distinctive peaks at diffraction angles 2θ=6.0°, 10.0°, 13.7°, 20.3° and 23.0° on a powder X-ray diffraction spectrum. Crystal C of Compound (a) also exhibits a pattern as shown in FIG. 7 on a powder X-ray diffraction spectrum.

Crystal C of Compound (a) exhibits an endothermic peak with an extrapolated onset temperature of 100° C. and 278° C. according to differential scanning calorimetry (DSC).

Figure 12:
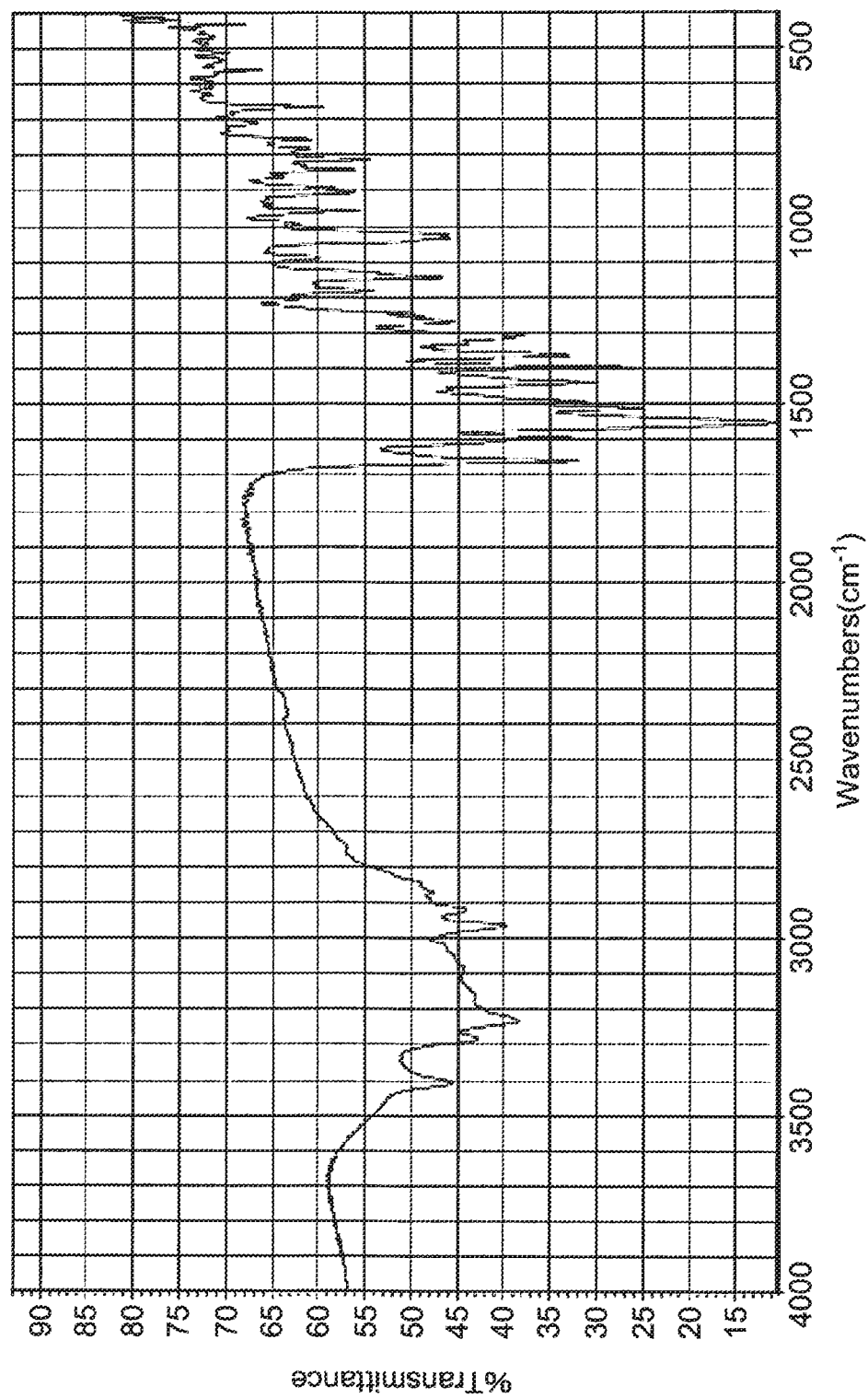
FIG. 12 is an infrared absorption spectrum of a crystal (Crystal C) of a solvate of 1-(6-((6-(((1R)-1-hydroxyethyl)-8-(isopropylamino)pyrido[3,4-d]pyrimidine-2-yl)amino)-3-pyridyl)piperazine-2-one with dimethyl sulfoxide.

Crystal C of Compound (a) exhibits absorption peaks at wave numbers of 840 cm$^{-1}$, 904 cm$^{-1}$, 955 cm$^{-1}$, 1490 cm$^{-1}$ and 3281 cm$^{-1}$ on an infrared absorption spectrum obtained according to the KBrtablet method. Crystal C of Compound (a) also exhibits an infrared absorption spectrum chart as shown in FIG. 12.

Figure 8:
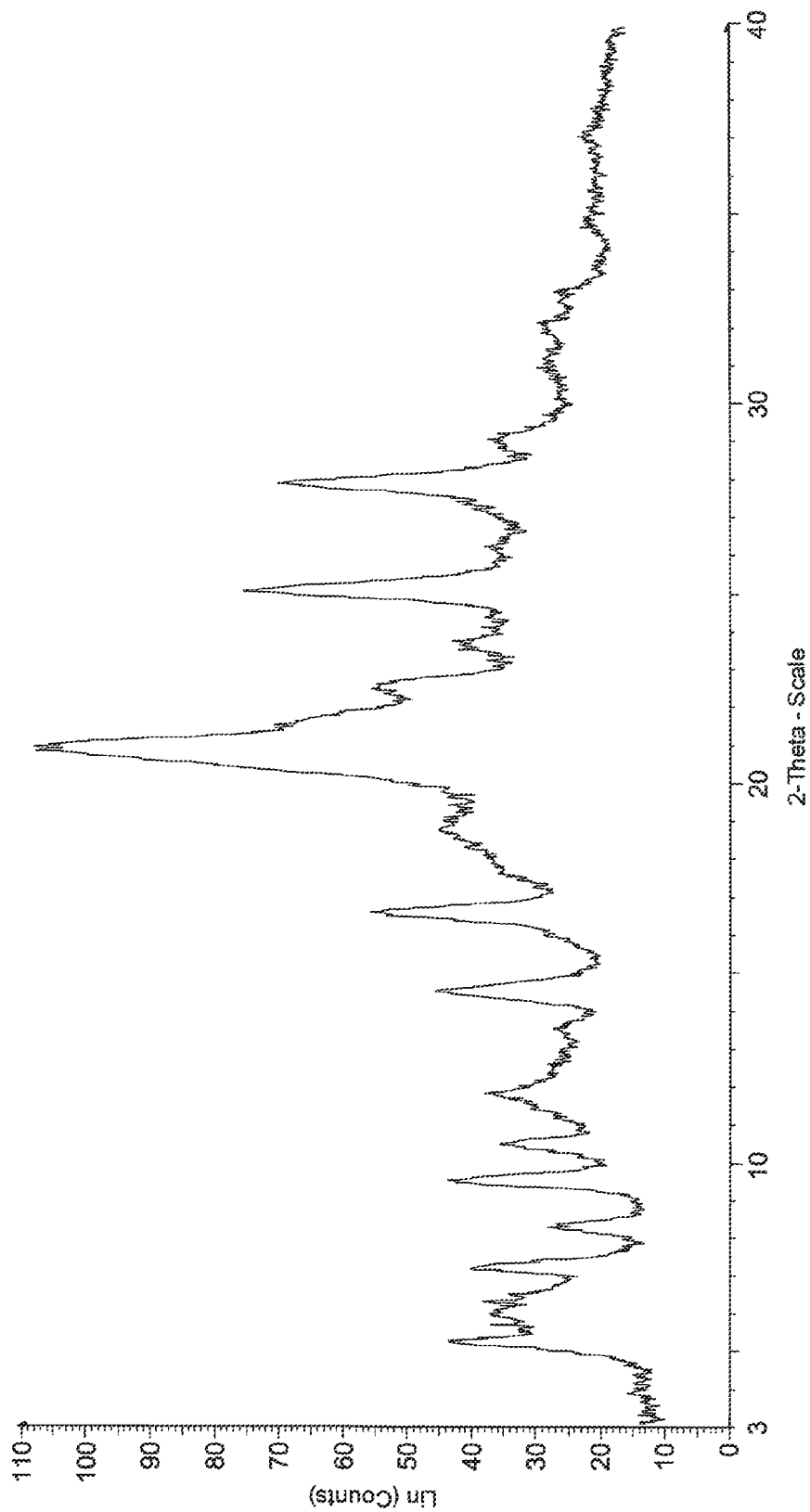
FIG. 8 is a powder X-ray diffraction spectrum of Crystal I of 1-(6-((6-(((1R)-1-hydroxyethyl)-8-(isopropylamino)pyrido[3,4-d]pyrimidine-2-yl)amino)-3-pyridyl)piperazine-2-one.

Crystal I of Compound (a) exhibits distinctive peaks at diffraction angles 2θ=5.2°, 7.2°, 9.5°, 14.5°, 16.5°, 20.9°, 25.0° and 27.9° on a powder X-ray diffraction spectrum. Crystal 1 of Compound (a) also exhibits a pattern as shown in FIG. 8 on a powder X-ray diffraction spectrum.

Crystal I of Compound (a) exhibits an endothermic peak with an extrapolated onset temperature of 272° C. according to differential scanning calorimetry (DSC).

Figure 13:
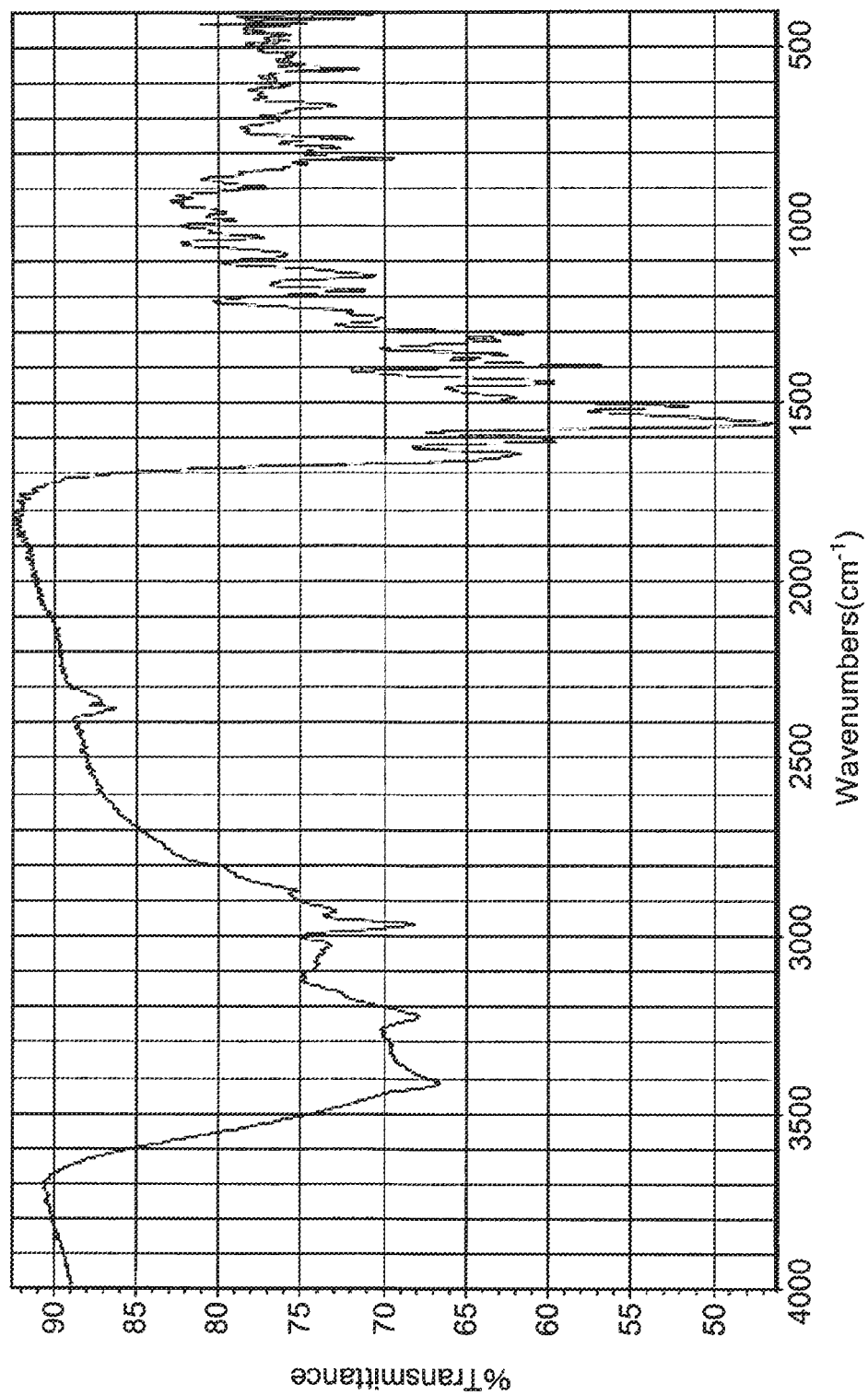
FIG. 13 is an infrared absorption spectrum of Crystal 1 of 1-(6-((6-(((1R)-1-hydroxyethyl)-8-(isopropylamino)pyrido[3,4-d]pyrimidine-2-yl)amino)-3-pyridyl)piperazine-2-one.

Crystal I of Compound (a) exhibits absorption peaks at wave numbers of 1081 cm$^{-1}$ and 1260 cm$^{-1}$ on an infrared absorption spectrum obtained according to the KBrtablet method. Crystal I of Compound (a) also exhibits an infrared absorption spectrum chart as shown in FIG. 13.

Figure 3:
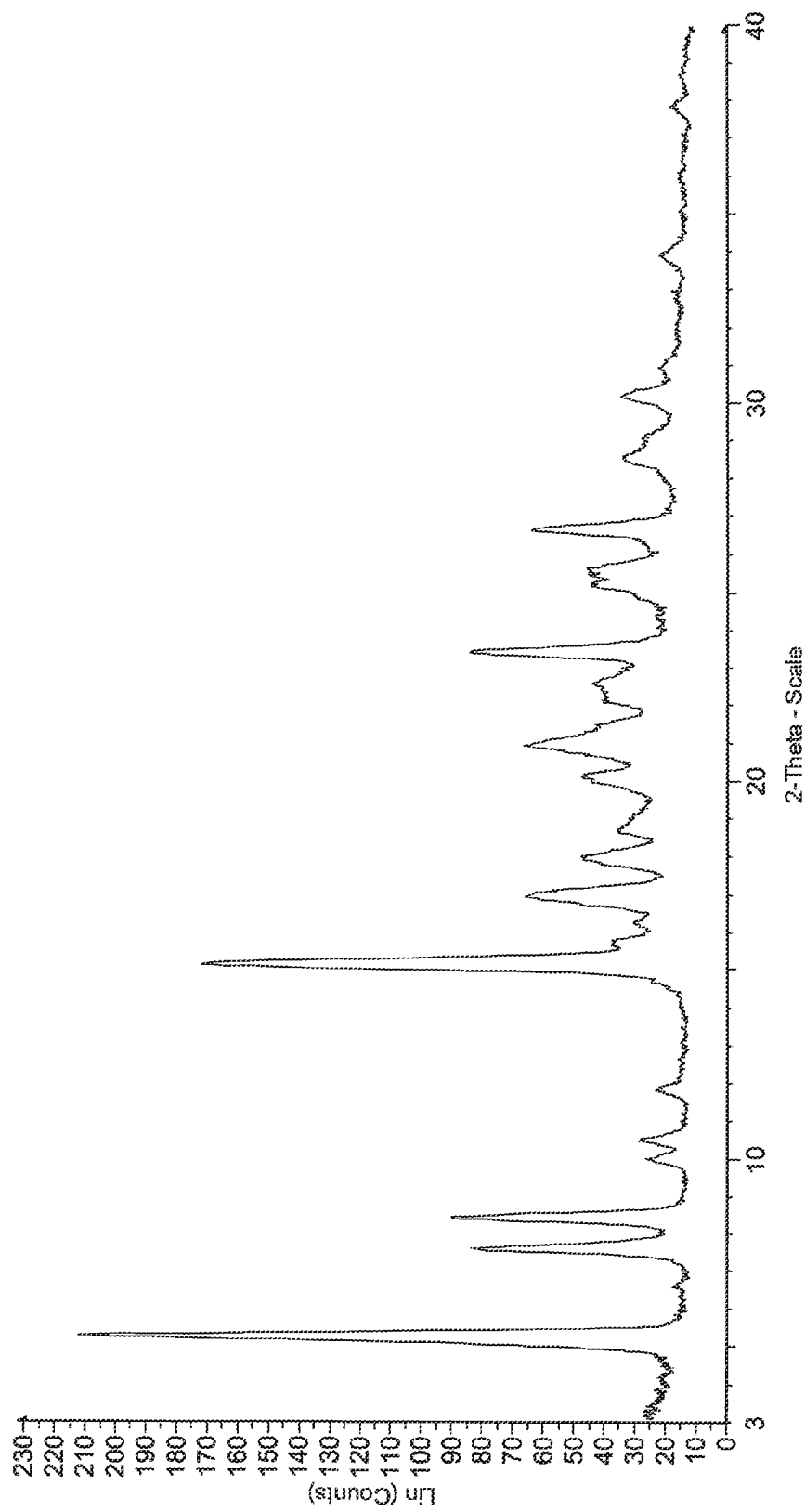
FIG. 3 is a powder X-ray diffraction spectrum of Crystal A of 1-(6-((6-(((1R)-1-methoxyethyl)-8-(isopropylamino)pyrido[3,4-d]pyrimidine-2-yl)amino)-3-pyridazyl)piperazine.

Crystal A of Compound (b) exhibits distinctive peaks at diffraction angles 2θ=5.2°, 7.6°, 8.4°, 10.5°, 15.2°, 16.9°, 20.1°, 21.0°, 23.3° and 26.6° on a powder X-ray diffraction spectrum. Crystal A of Compound (b) also exhibits a pattern as shown in FIG. 3 on a powder X-ray diffraction spectrum.

Crystal A of Compound (b) exhibits an endothermic peak with an extrapolated onset temperature of 225° C. according to differential scanning calorimetry (DSC).

Figure 14:
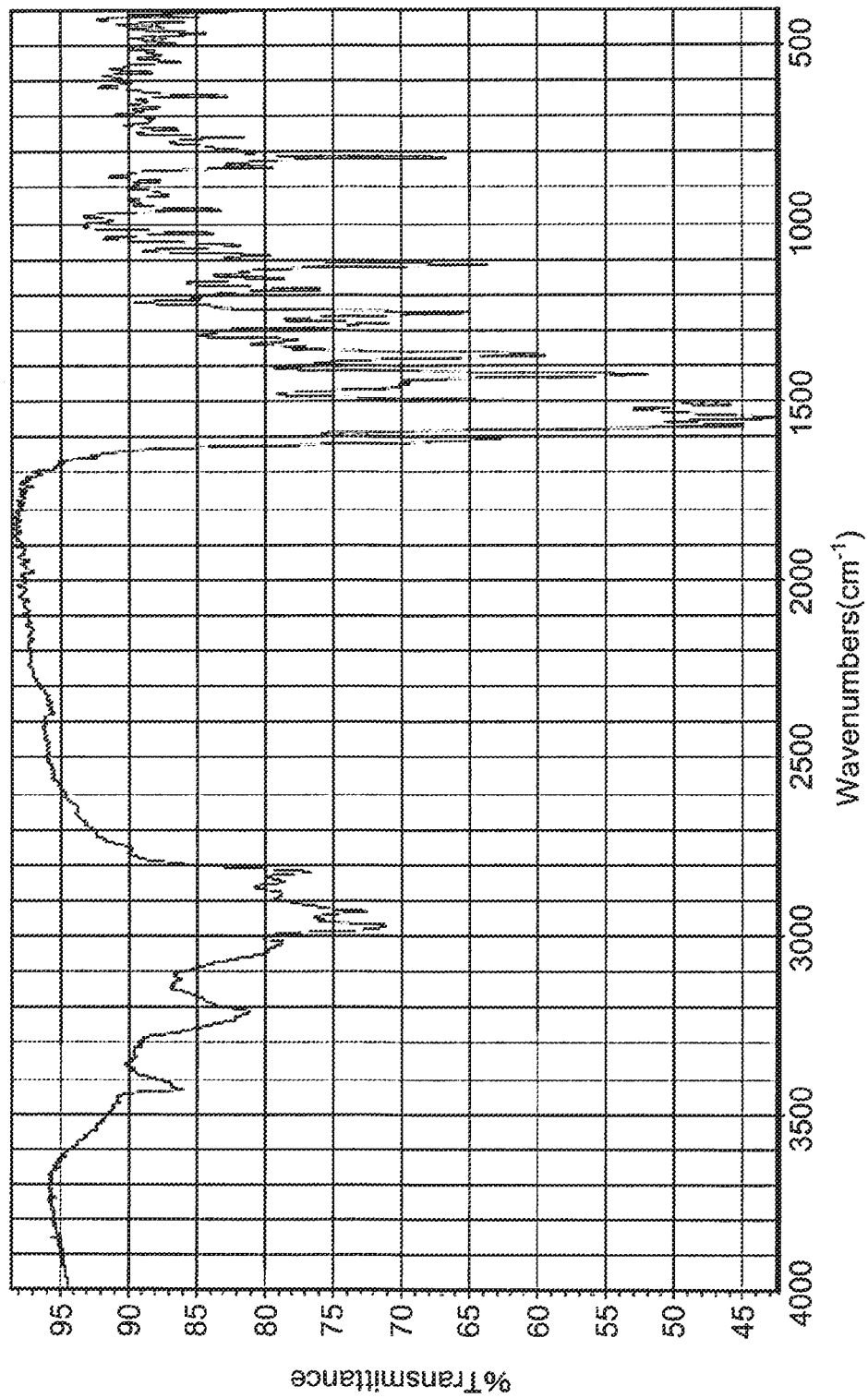
FIG. 14 is an infrared absorption spectrum of Crystal A of 1-(6-((6-(((1R)-1-methoxyethyl)-8-(isopropylamino)pyrido[3,4-d]pyrimidine-2-yl)amino)-3-pyridazyl)piperazine.

Crystal A of Compound (b) exhibits absorption peaks at wave numbers of 1369 cm$^{-1}$, 1424 cm$^{-1}$, 1508 cm$^{-1}$, 1545 cm$^{-1}$ and 1566 cm$^{-1}$ on an infrared absorption spectrum. Crystal A of Compound (b) exhibits an infrared absorption spectrum chart as shown in FIG. 14.

Figures 1, 21:
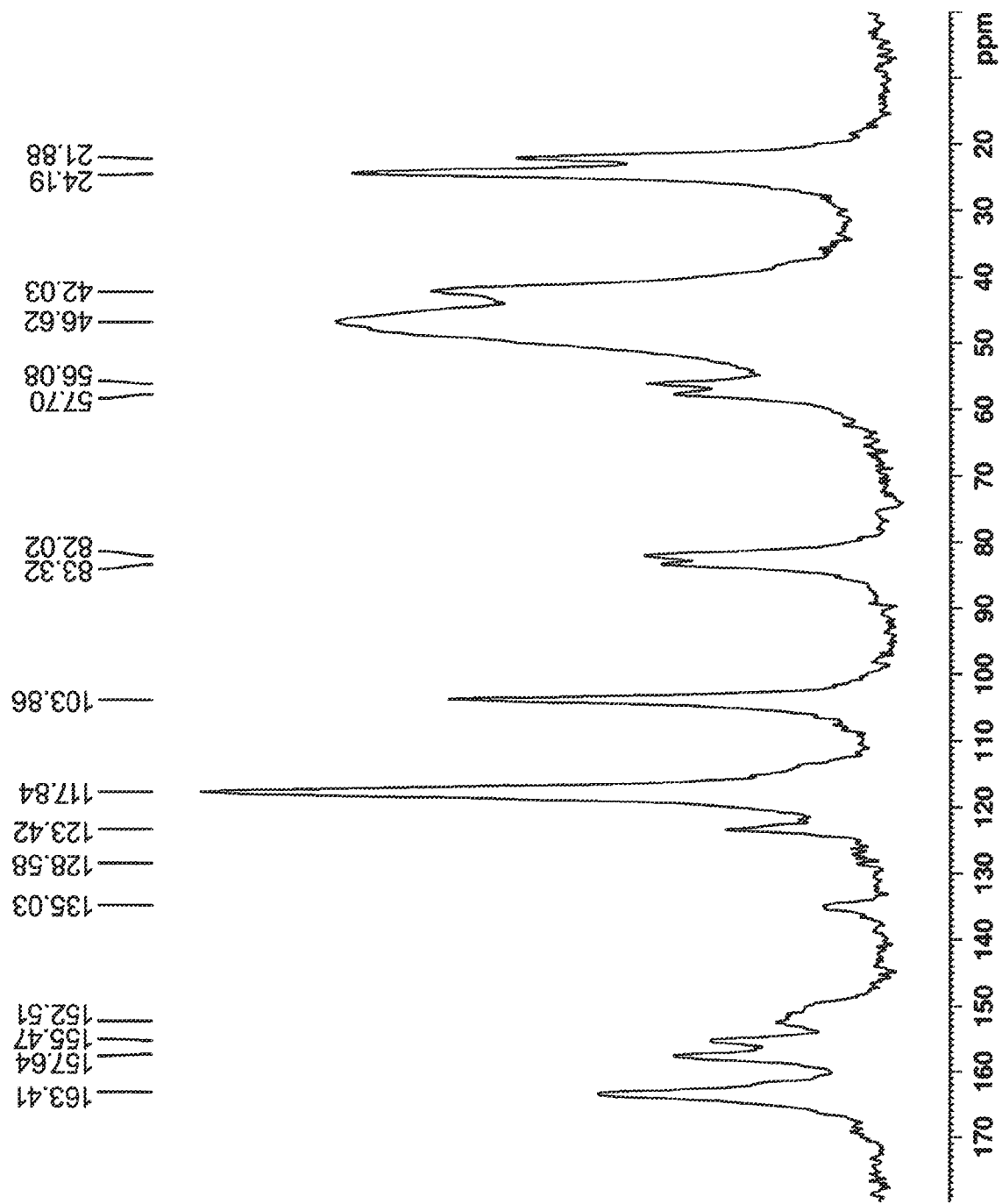
Figures 2, 21:
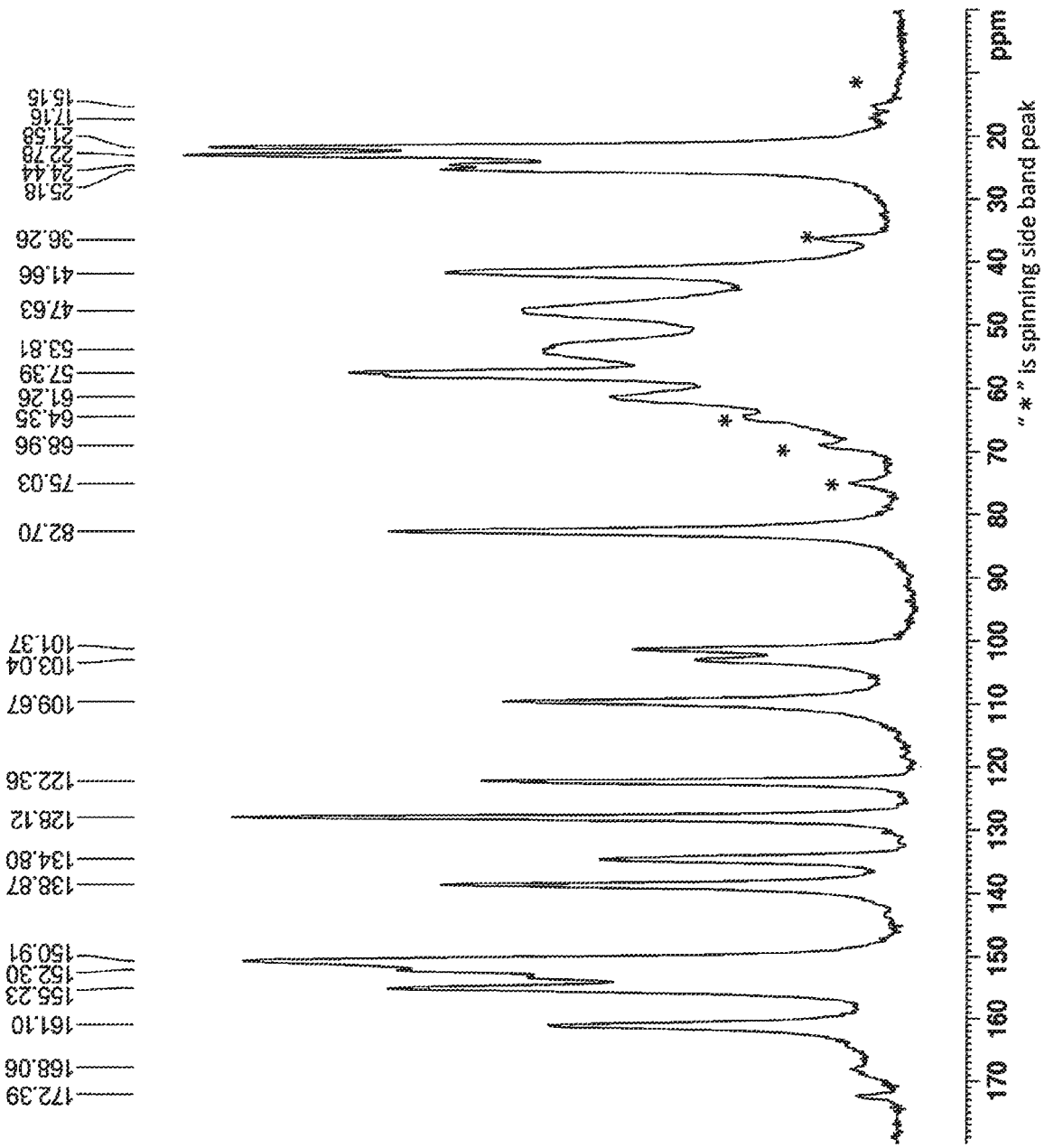

Crystal A of Compound (b) exhibits chemical shifts of 163.4 ppm, 157.6 ppm, 155.5 ppm, 117.8 ppm, 82.2 ppm, 56.1 ppm and 42.3 ppm on a $^{13}$C solid NMR spectrum. Crystal A of Compound (b) also exhibits a $^{13}$C solid NMR spectrum chart as shown in FIG. 21-1 (6500 Hz) and FIG. 21-2 (14000 Hz).

Figure 22:
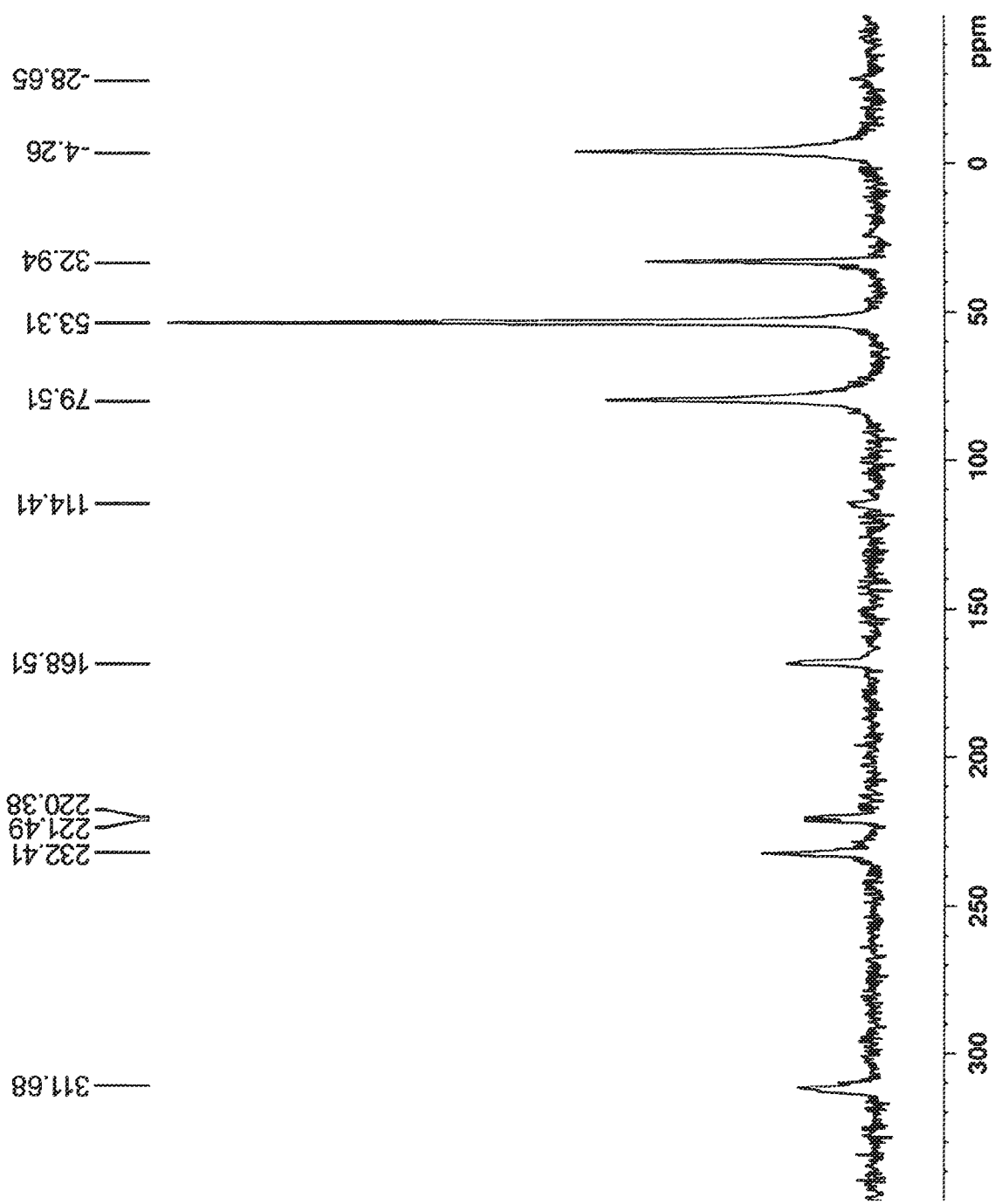
FIG. 22 is a solid NMR spectrum ($^{15}N$) of Crystal A of 1-(6-((6-(((1R)-1-methoxyethyl)-8-(isopropylamino)pyrido[3,4-d]pyrimidine-2-yl)amino)-3-pyridazyl)piperazine.

Crystal A of Compound (b) exhibits chemical shifts at 311.7 ppm, 232.4 ppm, 168.5 ppm, 79.5 ppm, 53.3 ppm, 32.9 ppm and −4.3 ppm on a $^{15}$N solid NMR spectrum. Crystal A of Compound (b) also exhibits a $^{15}$N solid NMR spectrum chart as shown in FIG. 22.

Figure 4:
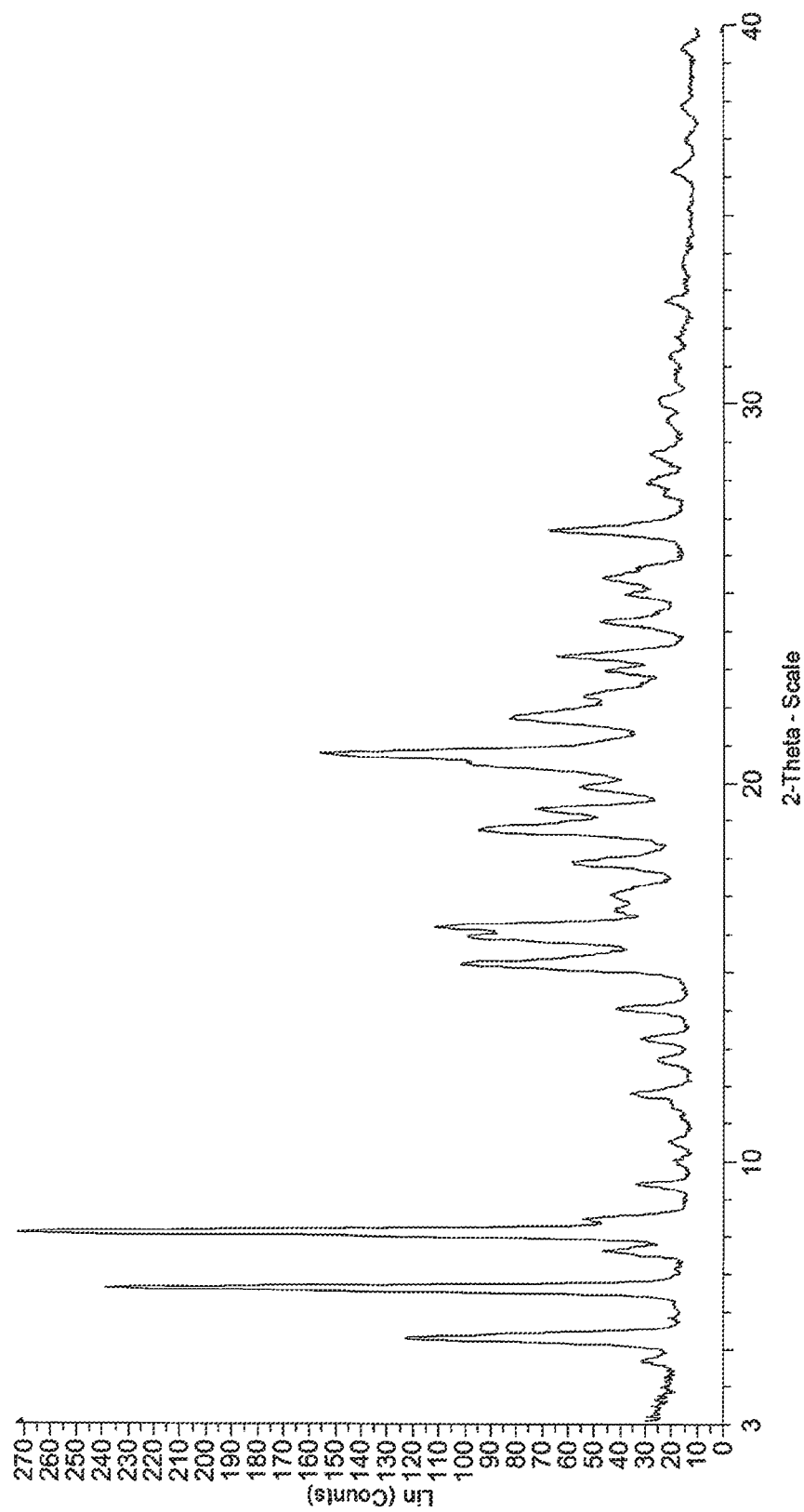
FIG. 4 is a powder X-ray diffraction spectrum of Crystal B of 1-(6-((6-(((1R)-1-methoxyethyl)-8-(isopropylamino)pyrido[3,4-d]pyrimidine-2-yl)amino)-3-pyridazyl)piperazine.

Crystal B of Compound (b) exhibits on a powder X-ray diffraction spectrum diffraction angle 2θ=5.2°, 6.6°, 8.1°, 15.2°, 15.9°, 16.2°, 18.8°, 20.5°, 20.8° and 21.7° distinctive peaks. Crystal B of Compound (b) exhibits a pattern as shown in FIG. 4 on a powder X-ray diffraction spectrum.

Crystal B of Compound (b) exhibits an endothermic peak with an extrapolated onset temperature of 221° C. according to differential scanning calorimetry (DSC).

Figure 9:
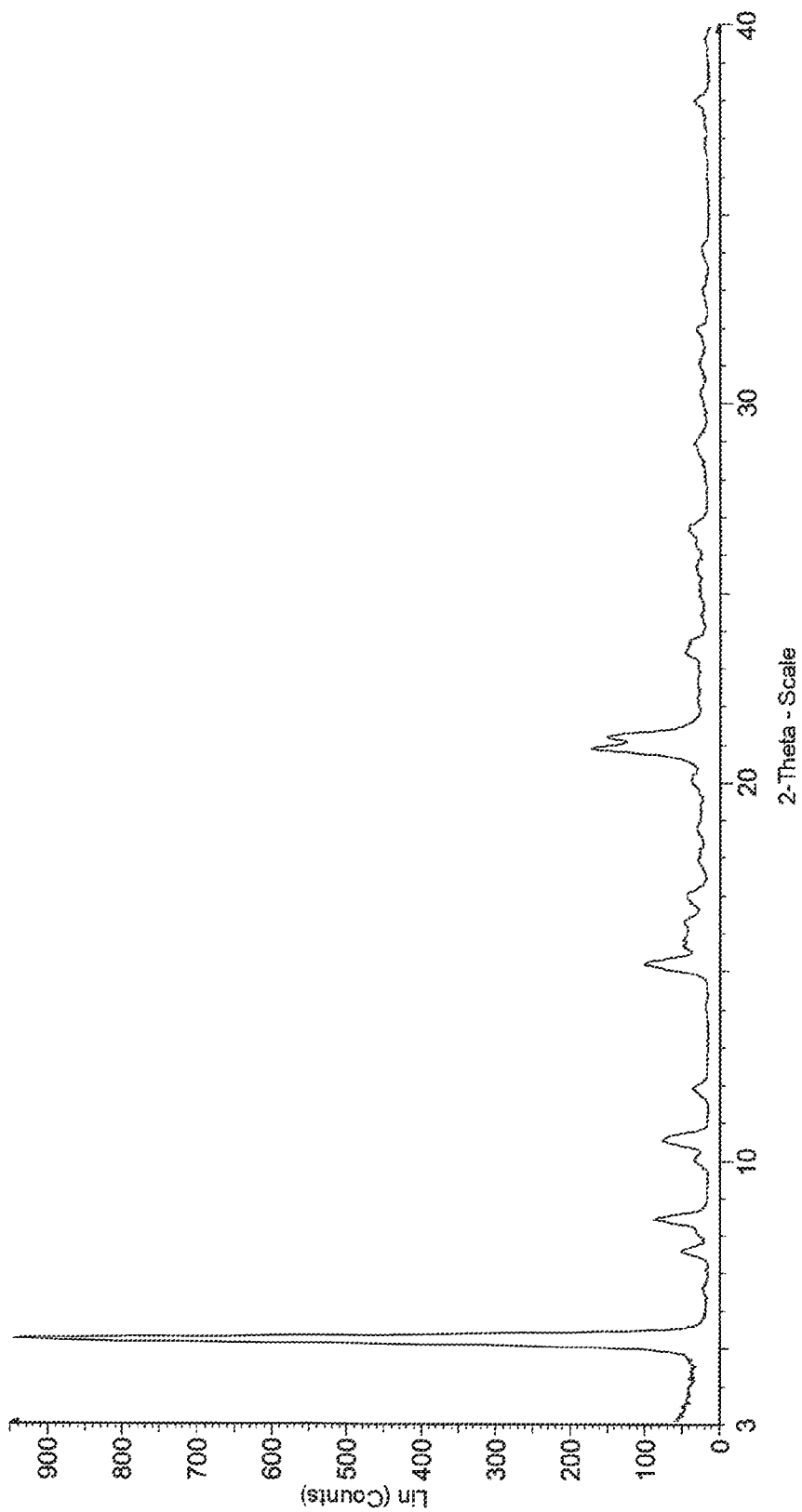
FIG. 9 is a powder X-ray diffraction spectrum of Crystal C of 1-(6-((6-(((1R)-1-methoxyethyl)-8-(isopropylamino)pyrido[3,4-d]pyrimidine-2-yl)amino)-3-pyridazyl)piperazine.

Crystal C of Compound (b) exhibits distinctive peaks at diffraction angles 2θ=5.2°, 7.6°, 8.4°, 10.0°, 10.5°, 11.9°, 15.2°, 17.0°, 20.9° and 21.2° on a powder X-ray diffraction spectrum. Crystal C of Compound (b) exhibits a pattern as shown in FIG. 9 on a powder X-ray diffraction spectrum. Crystal C of Compound (b) also exhibits an endothermic peak with an extrapolated onset temperature of 223° C. according to differential scanning calorimetry (DSC).

Figure 15:
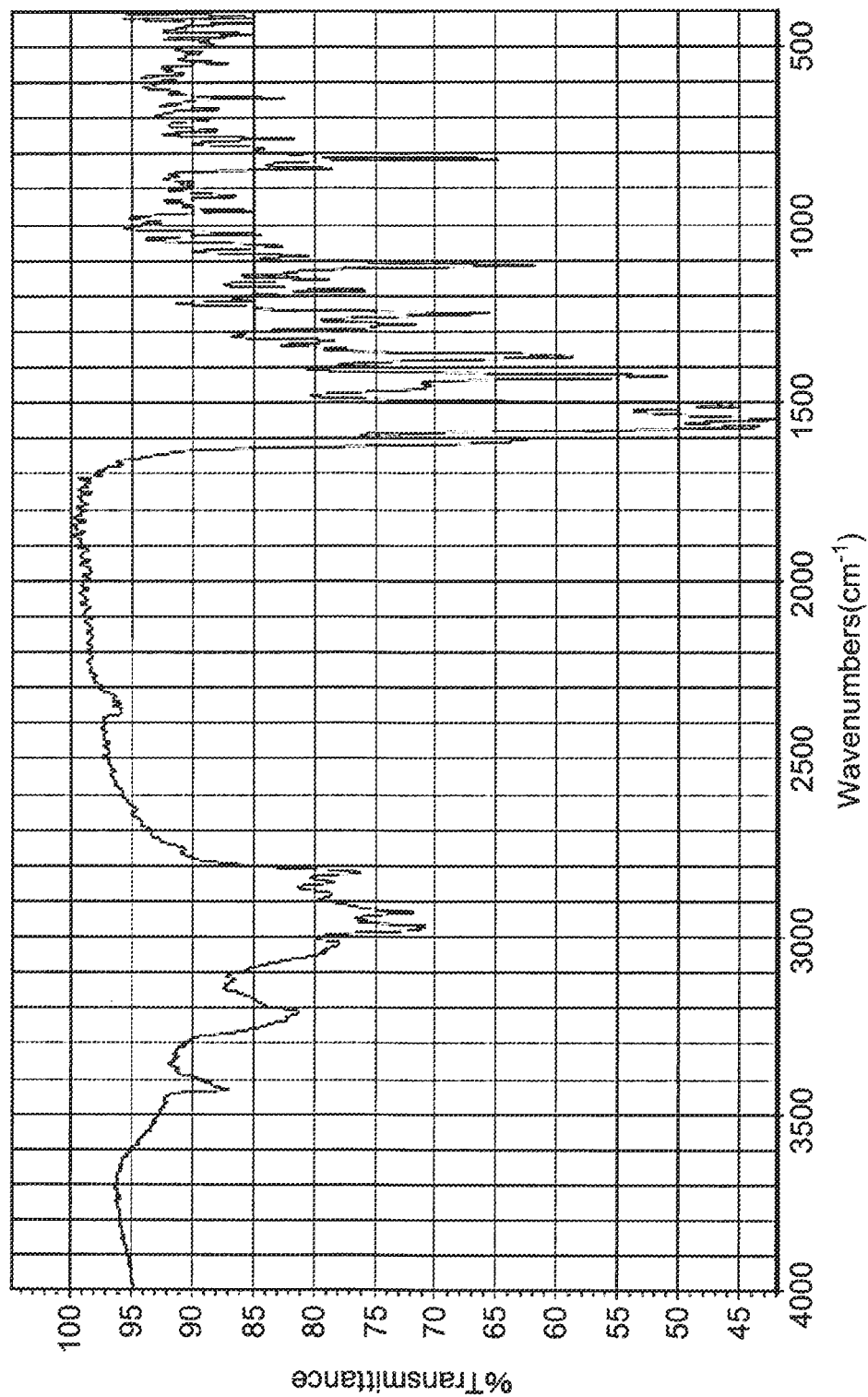
FIG. 15 is an infrared absorption spectrum of Crystal C of 1-(6-((6-(((1R)-1-methoxyethyl)-8-(isopropylamino)pyrido[3,4-d]pyrimidine-2-yl)amino)-3-pyridazyl)piperazine.

Crystal C of Compound (b) exhibits absorption peaks at wave numbers of 1369 cm$^{-1}$, 1424 cm$^{-1}$, 1507 cm$^{-1}$, 1546 cm$^{-1}$ and 1566 cm$^{-1}$ on an infrared absorption spectrum obtained according to the KBrtablet method. Crystal C of Compound (b) also exhibits an infrared absorption spectrum chart as shown in FIG. 15.

Figure 5:
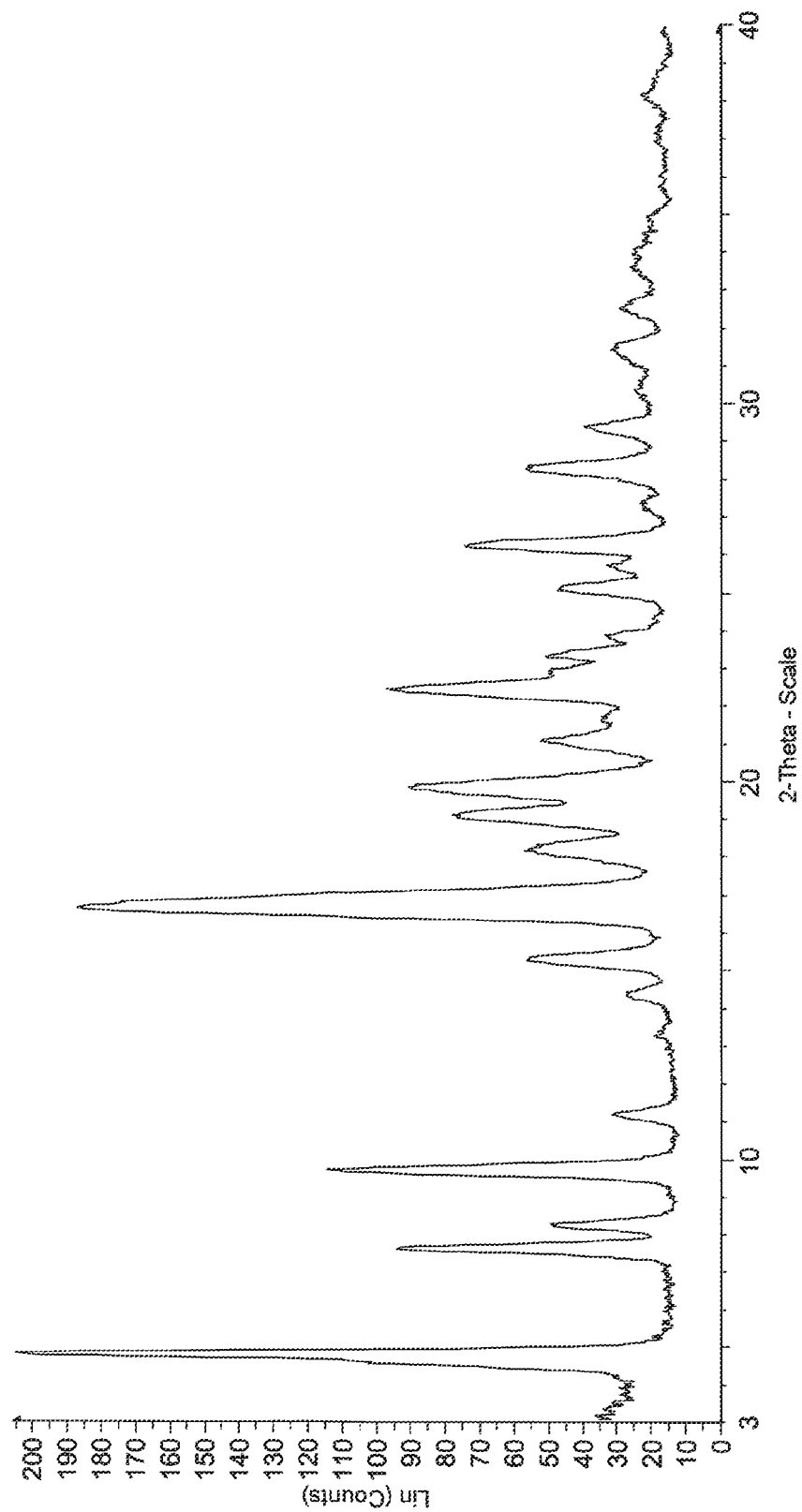
FIG. 5 is a powder X-ray diffraction spectrum of Crystal A of (R)—N8-isopropyl-6-(1-methoxyethyl)-N2-(5-(piperazine-1-ylmethyl)pyridin-2-yl)pyrido[3,4-d]pyrimidine-2,8-diamine.

Crystal A of Compound (c) exhibits on a powder X-ray diffraction spectrum 2θ=4.8°, 7.6°, 8.2°, 9.7°, 15.3°, 16.6°, 19.1°, 19.8°, 22.4° and 26.2° distinctive peaks. Crystal A of Compound (c) exhibits a pattern as shown in FIG. 5 on a powder X-ray diffraction spectrum.

Crystal A of Compound (c) exhibits an endothermic peak with an extrapolated onset temperature of 182° C. according to differential scanning calorimetry (DSC).

Figure 16:
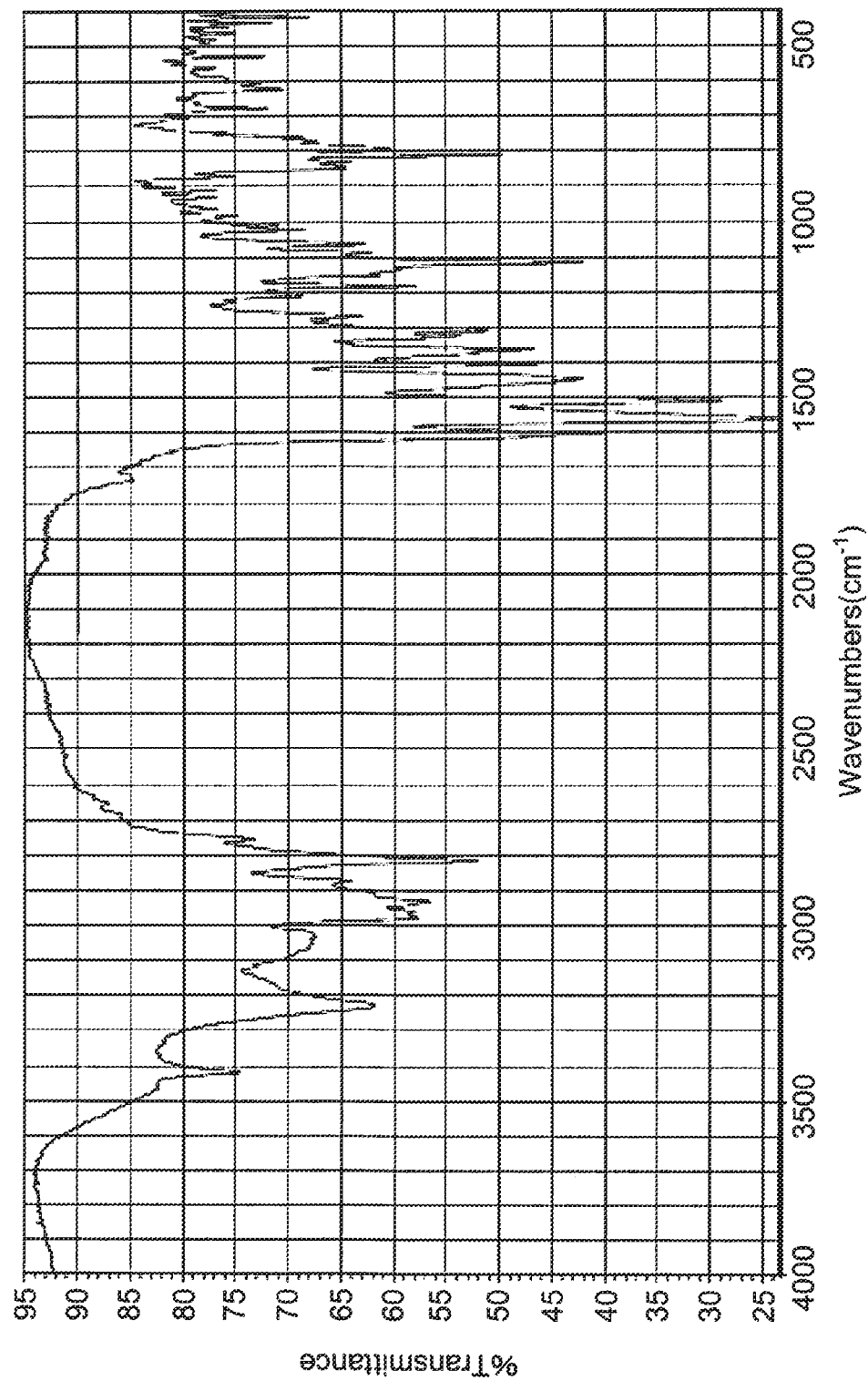
FIG. 16 is an infrared absorption spectrum of Crystal A of (R)—N8-isopropyl-6-(1-methoxyethyl)-N2-(5-(piperazine-1-ylmethyl)pyridin-2-yl)pyrido[3,4-d]pyrimidine-2,8-diamine.

Crystal A of Compound (c) exhibits absorption peaks at wave numbers of 1115 cm$^{-1}$, 1446 cm$^{-1}$, 1508 cm$^{-1}$, 1560 cm$^{-1}$ and 1601 cm$^{-1}$ on an infrared absorption spectrum obtained according to the KBrtablet method. Crystal A of Compound (c) e also exhibits an infrared absorption spectrum chart as shown in FIG. 16.

Figures 1, 23:
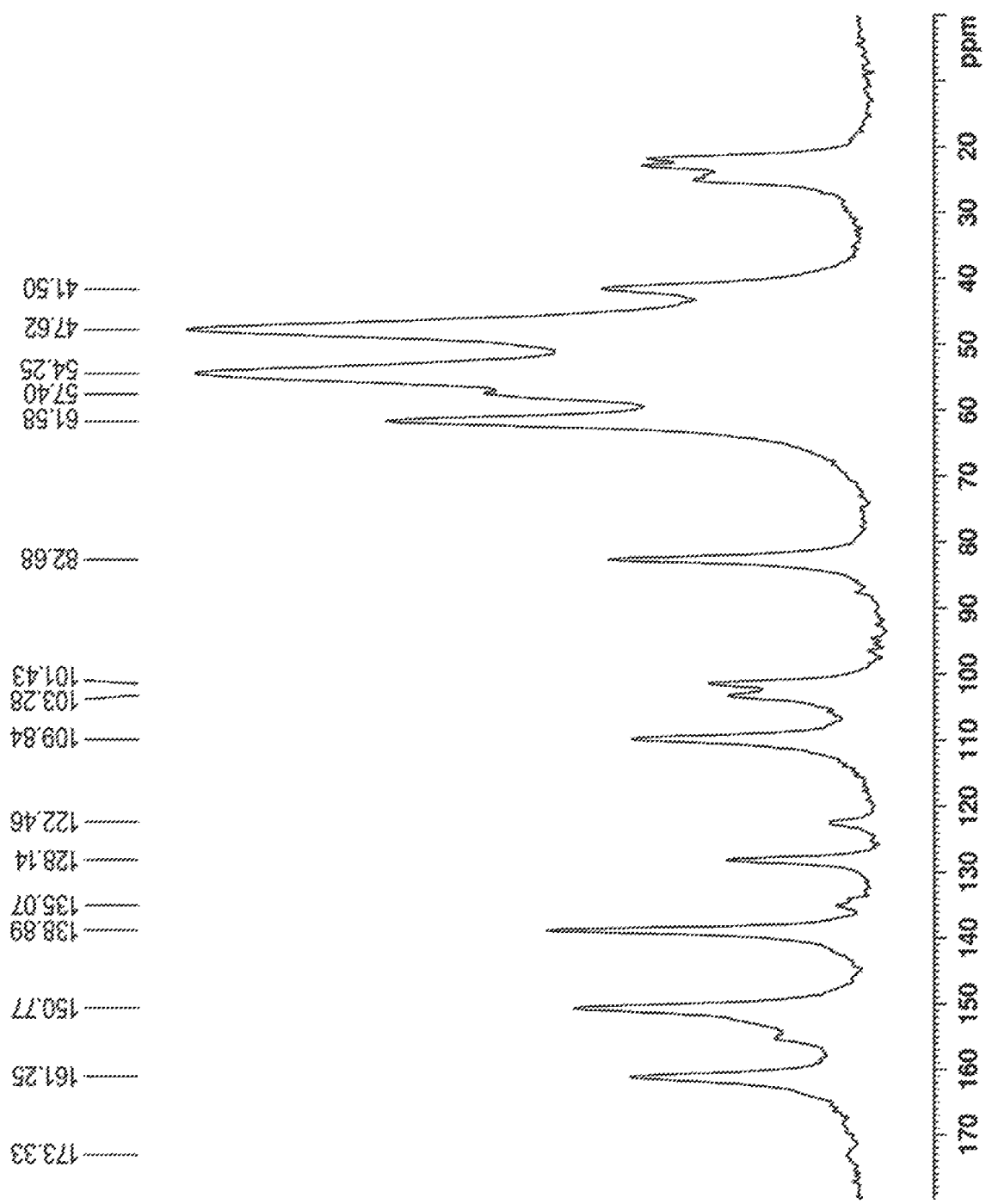
Figures 2, 23:
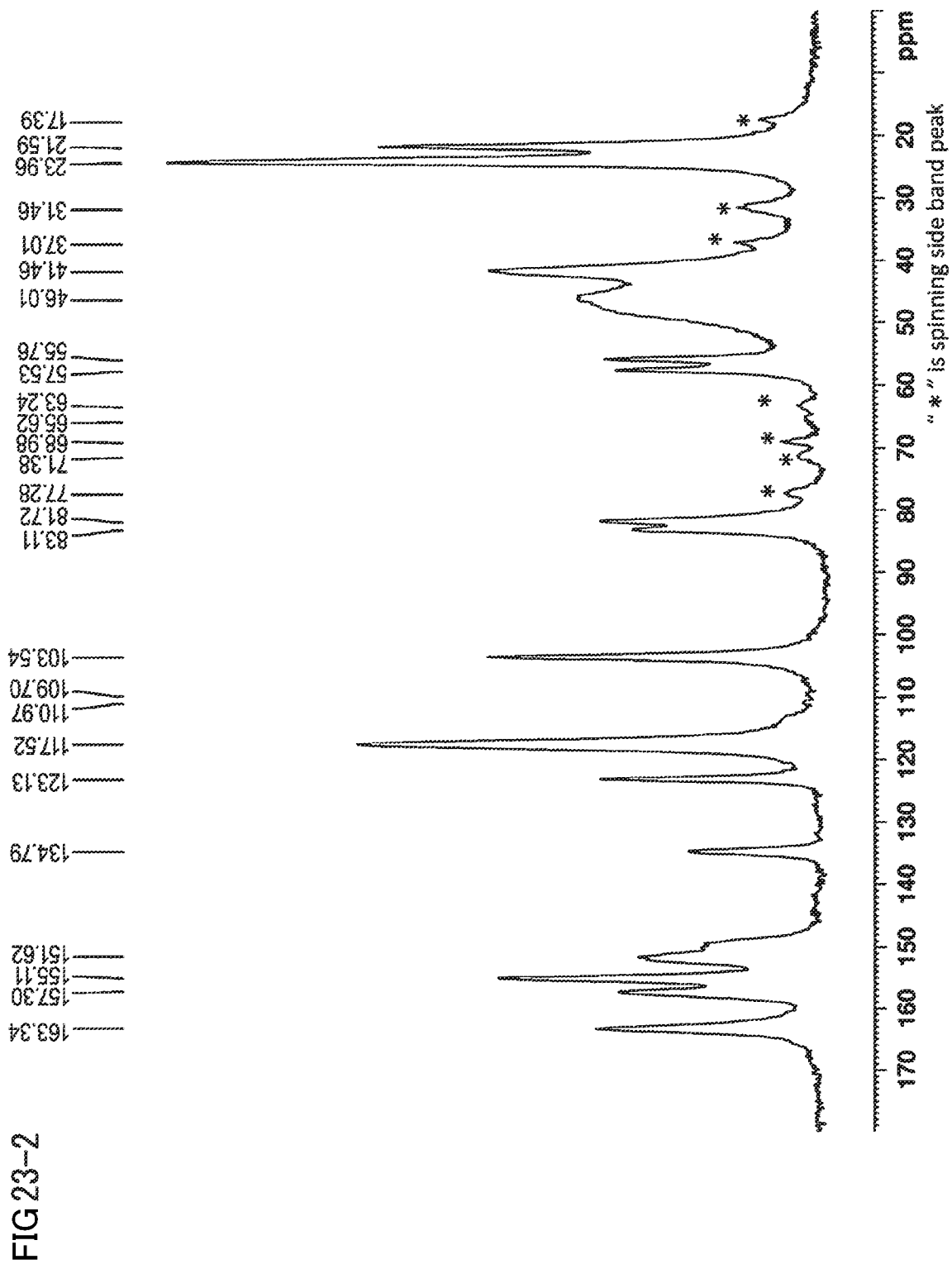

Crystal A of Compound (c) exhibits chemical shifts of 161.3 ppm, 150.8 ppm, 138.9 ppm, 128.1 ppm, 109.8 ppm, 82.7 ppm, 47.6 ppm, 42.5 ppm, 41.5 ppm, 24.5 ppm and 21.7 ppm on a $^{13}$C solid NMR spectrum. Crystal A of Compound (c) also exhibit a $^{13}$C solid NMR spectrum chart as shown in FIG. 23-1 (6500 Hz) and FIG. 23-2 (14000 Hz).

Figure 24:
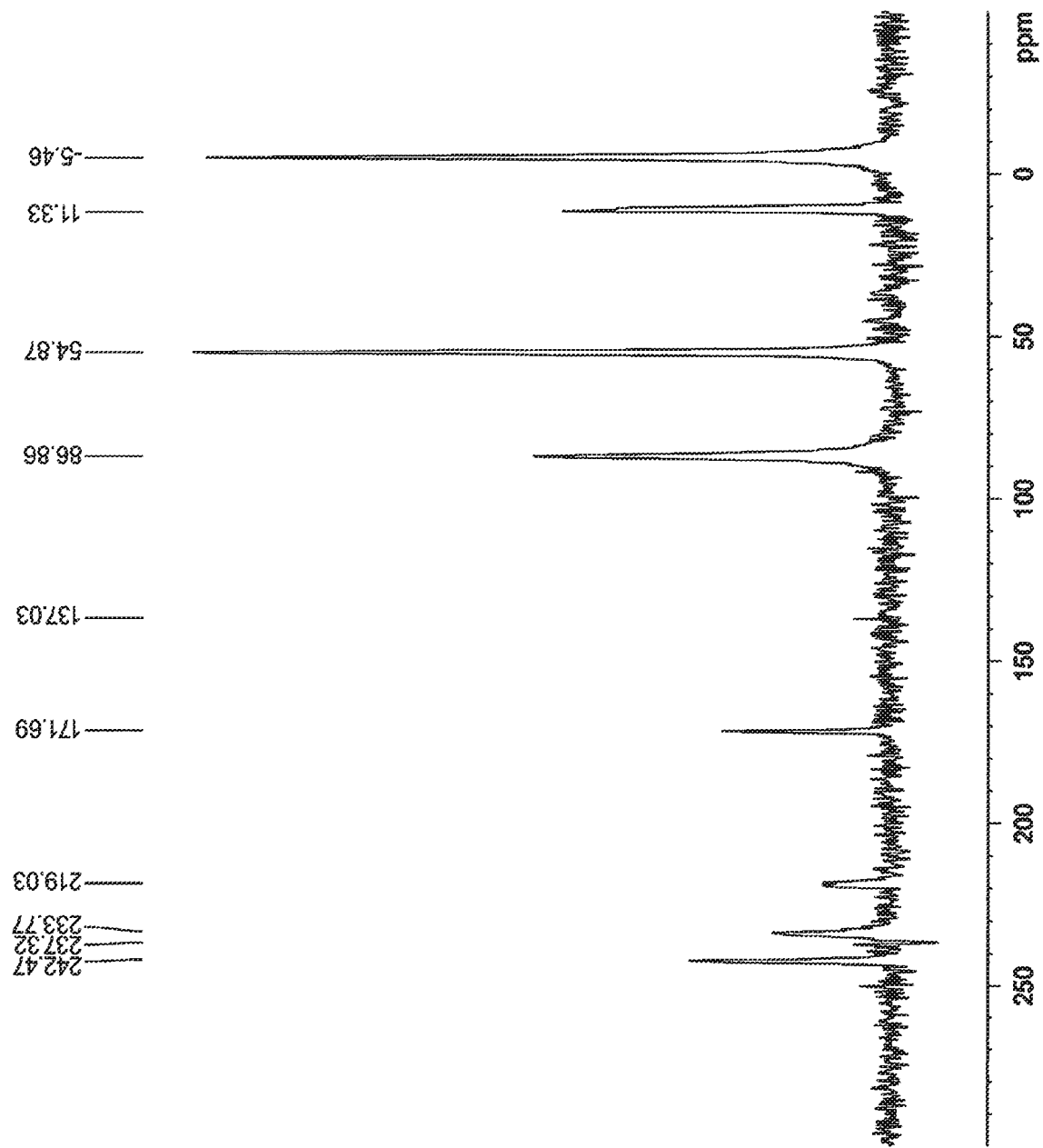
FIG. 24 is a solid NMR spectrum ($^{15}$N) of Crystal A of (R)—N8-isopropyl-6-(1-methoxyethyl)-N2-(5-(piperazine-1-ylmethyl)pyridin-2-yl)pyrido[3,4-d]pyrimidine-2,8-diamine.

Crystal A of Compound (c) exhibits chemical shifts at 242.8 ppm, 233.8 ppm, 219.0 ppm, 171.7 ppm, 86.9 ppm, 54.9 ppm, 11.3 ppm and −5.5 ppm on a $^{15}$N solid NMR spectrum. Crystal A of Compound (c) also exhibits a $^{15}$N solid NMR spectrum chart as shown in FIG. 24.

The term "distinctive peaks" used herein means peaks that are primarily observed for, and are characteristic of, each of the crystal polymorphs on a powder X-ray diffraction spectrum. Crystals identified by diffraction angles recited in the present invention may exhibit other peaks than the distinctive peaks.

The position and the relative intensity of each peak at a diffraction angle 2θ on a powder X-ray diffraction spectrum may somewhat vary depending on measurement conditions. Accordingly, identification of crystals should be determined based on the entire similarity of spectrum patterns, even though each 2θ value slightly differs. Crystals within the scope of error margin are encompassed by the present invention. An error margin of a 2θ value may be, for example, within a range of ±0.5° or ±0.2°. Namely, crystals having diffraction angles each within the range of ±0.2° to ±0.5° of the respective value mentioned above should be included in the scope of the crystal according to the present invention.

The crystals included within the scope of errors resulting from conditions for powder X-ray diffraction spectrometry (e.g., measuring instrument) are also encompassed by the present invention.

The term "extrapolated onset temperature" of a peak in the context of differential scanning calorimetry (DSC) means the temperature at which an exothermic or endothermic peak begins, i.e., an exothermic or endothermic onset temperature calculated via extrapolation. An exothermic or endothermic peak according to the differential scanning calorimetry (DSC) may somewhat vary depending on measurement conditions. An error margin may be, for example, within a range of ±5° C. or ±2° C. Namely, crystals having a peak within the range of ±2° C. to ±5° C. of the corresponding value mentioned above should be included in the scope of the crystal according to the present invention.

In general, chemical shifts on a solid NMR spectrum may also involve errors. An error margin of a chemical shift may be, for example, within a range of ±0.25 ppm, typically within a range of ±0.5 ppm. Namely, crystals having chemical shifts each within the range of ±0.25 ppm to ±0.5 ppm of the respective value mentioned above should be included in the scope of the crystal according to the present invention. Differences in, e.g., rotational frequencies and measurement instruments can affect the intensity or the occurrence/disappearance of each peak.

In general, absorption peaks on an infrared absorption spectrum may also involve errors. An error margin of an absorption peak may be, for example, within a range of ±2 cm$^{-1}$, typically within a range of ±5 cm$^{-1}$. Namely, crystals having absorption peaks each within the range of ±2 cm$^{-1}$ to ±5 cm$^{-1}$ of the respective value mentioned above should be included in the scope of the crystal according to the present invention.

In addition, for each of powder X-ray diffraction spectrometry, differential scanning calorimetry (DSC), infrared absorption spectrometry, $^{13}$C solid NMR spectrometry, and $^{15}$N solid NMR spectrometry, although there may be a difference between an actual measurement value of a reference standard for each crystal (e.g., a crystal obtained by the method described in the Examples of the present application the examples of the present specification) and the specific value mentioned above, such a difference should be accepted as an measurement error. Namely, crystals having diffraction angles, endothermic or exothermic peaks, infrared absorption spectra, $^{13}$C solid NMR spectra, or $^{15}$N solid NMR spectra that stays within the error range calculated in the manner mentioned above should be included in the scope of the crystal according to the present invention.

EXAMPLES

Examples in accordance with the disclosure will now be described by way of Examples. However, the following Examples should not be construed to limit the present invention. For example, the methods of synthesizing, purifying, and crystallizing compounds described in the following examples are mere embodiments for preparation of the crystal of the present invention, and thus the crystal of the present invention should not be limited to the crystal prepared by the methods of synthesizing, purifying, and crystallizing the compound disclosed in the following examples.

The structure of crystal compounds in accordance with Examples and novel compound s isolated during the synthesis were determined by $^1$H-NMR or mass spectrometry using LC/MS (liquid chromatograph/mass spectrometer).

The $^1$H-NMR was measured with JEOL JNM-ECZ400S (400 MHz). The standard sample was TMS (tetramethylsilane) (the peak at 0.0 ppm) for CDCl$_3$ solvent or dimethyl sulfoxide (the peak at 2.49 ppm) for DMSO-d6. With a $^1$H-NMR spectrum (400 MHz, DMSO-d$_6$, CD$_3$OD, or CDCl$_3$), the chemical shift (δ: ppm) and coupling constant (J: Hz) are shown, where s indicates singlet, d indicates doublet, t indicates triplet, q indicates quartet, brs indicates broad singlet, and m indicates multiplet.

The results of the LC/MS spectrometry are represented by [M+H]$^+$ (observed molecular weight (Obs. MS). i.e., proton [H]$^+$ is added to the molecular mass [M] of the compound).

The X-ray diffraction spectrum of the each crystalline powder in accordance with Examples was observed under the following conditions:
Instrument: D8 DISCOVER With GADDS CS made by Bulker AXS Inc., X-ray source: Cu.Kα (wavelength: 1.541838 (10$^{-10}$ m)), tube voltage-tube current: 40 kv-40 mA, incident-side flat plate graphite monochromator, collimator: ϕ300 μm, two-dimensional PSPC detector, scan rage: 3 to 40°.

The differential scanning calorimetry of the samples in Examples was performed under the following conditions:
Instrument: DSC 8000 made by Perkin Elmer, heating rate: 10° C./min, atmosphere: nitrogen, sample pan: aluminum, sampling: 0.1 sec, scanning range: 25 to 300° C.

The IR absorption spectrum (KBr) of each sample in Examples was observed in accordance with a potassium bromide tablet procedure in the IR absorption spectrometry described in the general testing methods Japanese Pharmacopoeia under the following conditions:
Instrument: AVATAR320 Nicolet iS5 made by Thermo Fisher Scientific, Scanning range: 4000 to 400 cm$^{-1}$, resolution: 4 cm$^{-1}$, accumulation runs: 16.

The solid NMR spectrum of each sample in Examples was observed under the following conditions:
Instrument: Bruker DSX300WB, measured nuclei: $^{13}$C and $^{15}$N, pulse repetition time: 5 s, pulse mode: CP/MAS.

Example 1

Example 1 describes Crystal D of 1-(6-(((6-(((1R)-1-hydroxyethyl)-8-(isopropylamino)pyrido[3,4-d]pyrimidin-2-yl) amino)-3-pyridyl)piperazin-2-one (Compound (a)).
Synthesis of Compound (a) will be described.

<Synthesis of Compound (a)-1>
Methyl 5-bromo-2-methylthiopyrimidine-4-carboxylate (Compound (a)-1) was synthesized.

[Chemical formula 2]

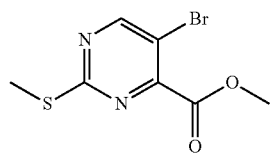

((a)-1)

A solution of 5-bromo-2-(methylthio)pyrimidine-4-carboxylic acid (110 g, 0.44 mol) in methanol (1.1 L) was cooled to 0° C. with stirring, and then thionyl chloride (50 mL, 0.66 mol) was added dropwise. The solution was slowly heated to reflux for four hours. The completion of the reaction was confirmed by LC/MS and TLC, the solution was cooled to room temperature. The volatile component was removed under reduced pressure, and the residue was dissolved in ethyl acetate (1 L). The solution was washed with aqueous 10% sodium carbonate solution (200 mL) three times and with saturated brine (200 mL) two times. The resulting organic phase was dried over magnesium sulfate anhydride. After the solid component was filtered out, the filtrate was concentrated. The crude product was purified by silica gel column chromatography to Compound (a)-1 (88 g, 75%).

<Synthesis of Compound (a)-2>
Compound (a)-2, 5-bromo-2-methylthiopyrimidine-4-carbaldehyde, was synthesized.

[Chemical formula 3]

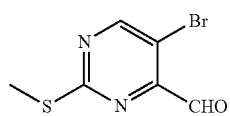

((a)-2)

A 1.7 M solution of Compound (a)-1 (25 g, 95 mmol) in THF (tetrahydrofuran) (375 mL) was cooled with stirring to −78° C. in a nitrogen stream. Diisobutylaluminum hydride (84 mL, 143 mmol) in toluene was added dropwise to the solution, and the mixture was stirred for four hours at −78° C. After the completion of the reaction was confirmed by TLC, methanol was added dropwise at −78° C. to quench the reaction, and then the solution was slowly heated to 0° C. The solution was diluted with ethyl acetate and was suction-filtrated through a Celite pad. The filtrate was washed with saturated brine (200 mL) two times, the resulting organic phase was dried over magnesium sulfate anhydride, and then the solid component was filtered out. The filtrate was concentrated to give a titled compound (25 g, crude compound). The crude compound was used in the following reaction without further purification.

<Synthesis of Compound (a)-3>
Compound (a)-3, (R)-3-(4-formyl-2-methylthiopyrimidine-5-yl)-1-methyl-2-propynyl benzoate, was synthesized.

[Chemical formula 4]

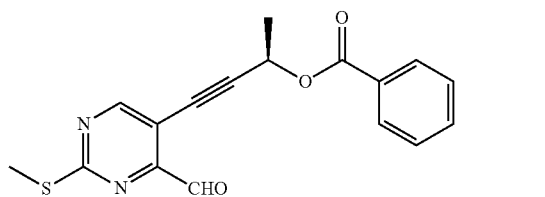

((a)-3)

A solution of PdCl$_2$(PPh$_3$)$_2$Cl$_2$ (7.832 g, 11.2 mmol) and copper iodide (2.12 g, 11.2 mmol) in 1,4-dioxane (60 ml) was deaerated and purged with argon. Diisopropylethylamine (25.29 mL, 145.1 mmol) was added at room temperature. The solution was stirred for five minutes at room temperature, and a solution of a mixture (26.0 g, crude compound) of Compound (a)-2 and (5-bromo-2-methylthiopyrimidin-4-yl)methoxymethanol in 1,4-dioxane (50 mL) was added at room temperature. A solution of (R)-1-methylpropargyl benzoate (23.3 g, 133.9 mmol) in 1,4-dioxane (55 mL) was then gradually added dropwise, and the solution was stirred for 16 hours at room temperature. The reaction was traced by LC/MS. After the completion of the reaction, the mixture was diluted with ethyl acetate (400 mL), and suction-filtrated through a Celite pad. The Celite pad was washed with ethyl acetate. The filtrate was concentrated under reduced pressure. The resulting crude produce was used in the following reaction without purification.

Synthesis of a mixture of Compound (a)-2 and (5-bromo-2-methylthiopyrimidin-4-yl)methoxymethanol will be described in Reference Example 1.

Reference Example 1

Synthesis of Mixture of Compound (a)-2 and (5-bromo-2-methylthiopyrimidin-4-yl)methoxymethanol

[Chemical formula 5]

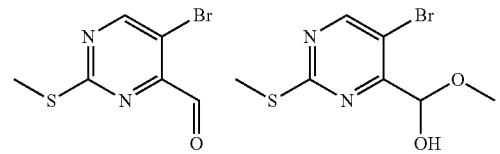

A solution of Compound (a)-2 (25 g, 95 mmol) in THF (375 mL) was cooled with stirring to −78° C. in a nitrogen stream. A 1.7 M solution of diisobutyl aluminum hydride (84 mL, 143 mmol) in toluene was added dropwise and the solution was stirred for four hours at −78° C. After the completion of the reaction was confirmed by TLC, methanol was added dropwise at −78° C. to quench the reaction. The solution was slowly heated to 0° C. The solution was diluted with ethyl acetate, and was suction-filtrated through a Celite pad. The filtrate was washed with saturated brine (200 mL) two times, and the resulting organic phase was dried over magnesium sulfate anhydride. The solid component was filtered out. The filtrate was concentrated into the mixture (25 g, crude compound) of the titled compound. The crude product was used in the following reaction without further purification.

<Synthesis of Compound (a)-4>
Compound (a)-4, (R)-6-(1-(benzoyloxy)ethyl)-2-(methylthio)pyrido[3,4-d]pyrimidin-7-oxide, was synthesized.

[Chemical formula 6]

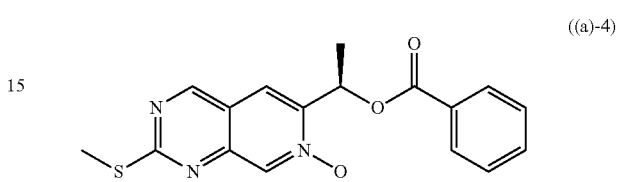

((a)-4)

Hydroxyamine monohydrochloride salt (8.31 g, 119.6 mmol) and sodium acetate (9.81 g, 119.6 mmol) was added to a solution (260 ml) of Compound (a)-3 (26.0 g, 79.8 mmol) in ethanol at room temperature, and the mixture was stirred 16 hours at room temperature. Ethanol (250 ml) was added to the solution, and potassium carbonate (27.5 g, 199.4 mmol) was added at room temperature, and the mixture was stirred for three hours at 50° C. The reaction was traced by LC/MS. After the completion of the reaction, the reaction mixture was suction-filtrated through a Celite pad. The Celite pad was washed with ethyl acetate (1.0 L) and a small volume of methanol. The filtrate was concentrated under reduced pressure, and the organic layer was dried over magnesium sulfate anhydride. The solid component was filtered out. The resulting crude product was purified by silica gel column chromatography to give Compound (a)-4 (13.0 g, 48%).

$^1$H-NMR spectrum of Compound (a)-4 is as follows:
$^1$H-NMR (CDCl$_3$) δ: 9.04 (1H, s), 8.79 (1H, s), 8.14 (2H, d, J=7.5 Hz), 7.77-7.40 (4H, m), 6.66 (1H, q, J=6.3 Hz), 2.65 (3H, s), 1.79 (3H, d, J=6.6 Hz)

<Synthesis of Compound (a)-5>
Compound (a)-5, (R)-1-(8-chloro-2-(methylthio)pyrido [3,4-d] pyrimidin-6-yl)ethyl benzoate was synthesized.

[Chemical formula 7]

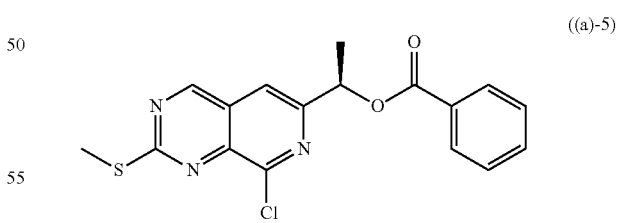

((a)-5)

Thionyl chloride (51 ml, 704 mmol) was added dropwise to a solution (130 ml) of Compound (a)-4 (8.0 g, 23.5 mmol) in dichloromethane at 0° C. in a nitrogen stream. The solution was stirred for 16 hours at room temperature. The reaction was traced by thin layer chromatography (TLC). After the completion of the reaction, the solution was concentrated under reduced pressure, and the resulting organic phase was purified by alumina column chromatography to give Compound (a)-5 (3.2 g, 37%).

¹H-NMR spectrum of Compound (a)-5 is as follows:

¹H-NMR (CDCl₃) δ: 9.19 (1H, s), 8.16-8.12 (2H, m), 7.68 (1H, s), 7.64-7.58 (1H, m), 7.53-7.46 (2H, m), 6.27 (1H, q, J=6.8 Hz), 2.74 (3H, s), 1.81 (3H, d, J=6.4 Hz)

<Compound (a)-6>

Synthesis of Compound (a)-6, (R)-1-(8-(isopropylamino)-2-(methylthio)pyrido[3,4-d]pyrimidin-6-yl)ethyl Benzoate

[Chemical formula 8]

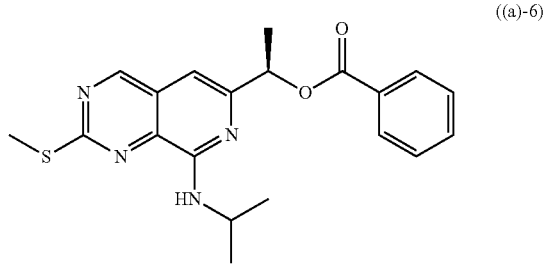

A mixture of Compound (a)-5 (3.06 g, 8.5 mmol) and isopropylamine (18 mL) was stirred for one hour at 80° C., and the solution was then cooled to room temperature. The solution was diluted with water, and subjected to extraction with ethyl acetate. The resulting organic phase was washed with brine, and then dried over sodium sulfate anhydride. The solvent was removed, and the crude product was purified by silica gel column chromatography to give Compound (a)-6 (1.78 g, yield 55%).

¹H-NMR spectrum of Compound (a)-6 is as follows:

¹H-NMR (DMSO-d₆) δ: 9.28 (1H, s), 8.08 (2H, d, J=7.4 Hz), 7.70 (1H, t, J=7.4 Hz), 7.57 (2H, t, J=7.7 Hz), 7.05 (1H, d, J=8.0 Hz), 6.99 (1H, s), 5.34 (2H, s), 4.32 (1H, m), 2.66 (3H, s), 1.25 (6H, d, J=6.5 Hz)

<Synthesis of Compound (a)-7>

Compound (a)-7, (R)-1-(8-(isopropylamino)-2-(methylsulfonyl)pyrido[3,4-d]pyrimidin-6-yl)ethyl benzoate, was synthesized.

[Chemical formula 9]

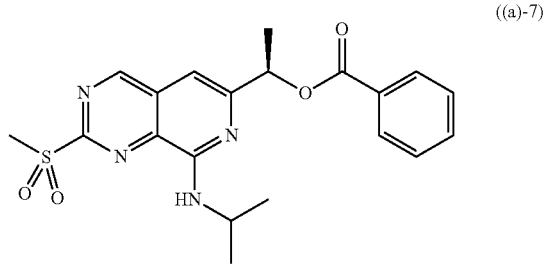

Oxone (peroxymonopotassium sulfate) (5.72 g, 9.3 mmol) was added to a solution of Compound (a)-6 (1.78 g, 4.7 mmol) in mixed solvent of tetrahydrofuran (47 ml) and water (47 ml) at 0° C., and the mixture was stirred for 18 hours at room temperature. The solution was subjected to extraction with ethyl acetate. The organic phase was washed with water, and was dried over anhydrous sodium sulfate. The solvent was removed and the crude produce was purified by silica gel column chromatography to give Compound (a)-7 (1.61 g, yield 87%). LC/MS: (M+H)⁺=415.0

<Synthesis of Compound (a)-8>

Compound (a)-8, tert-butyl 4-(6-nitropyridin-3-yl)-3-oxopiperazine-1-carboxylate was synthesized.

[Chemical formula 10]

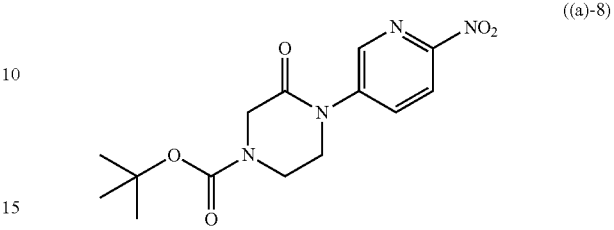

2-Nitro-5-bromopyridine (1.01, 5.0 mol), tert-butyl 2-oxo-4-piperazin-carboxylate (1.00, 5.0 mol), and cesium carbonate (3.26 g, 10.0 mmol) were suspended in 1,4-dioxane, and nitrogen gas was bubbled into the suspension for 30 minutes. Xantphos (4,5'-bis(diphenylphosphino)-9,9'-dimethylxanthene) 246 mg, 0.43 mmol) and tris(dibenzylideneacetone)dipalladium (229 mg, 0.25 mmol) was added to the suspension, and the mixture was heated to reflux with stirring for two hours. The solution was cooled to room temperature, and water and ethyl acetate were added. The solution was filtrated through a Celite pad. The organic layer of the filtrate was isolated, and the aqueous phase was extracted with ethyl acetate. The resulting organic phases were combined, and then dried over anhydrous sodium sulfate. The solid component was filtered out and the filtrate was concentrated under reduced pressure. The residue was purified by silica gel column chromatography to give Compound (a)-8 (1.08 g, 67%).

¹H-NMR (CDCl₃) δ: 8.67 (1H, d, J=2.4 Hz), 8.32 (1H, d, J=8.8 Hz), 8.15 (1H, dd, J=8.8, 2.4 Hz), 4.33 (2H, s), 3.93-3.83 (4H, m), 1.51 (9H, s)

<Synthesis of Compound (a)-9>

Compound (a)-9, tert-butyl 4-(6-aminopyridin-3-yl)-3-oxopiperazine-1-carboxylate, was synthesized.

[Chemical formula 11]

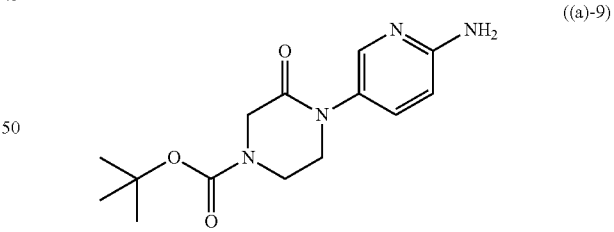

Compound (a)-8 (1.08 g, 3.34 mmol) was dissolved in a mixture of ethanol (45 mL) and THF (22 mL). Palladium on carbon (108 mg) was added to the solution, and the mixture was stirred for 24 hours in a hydrogen atmosphere. The solution was filtrated through a Celite pad, and the filtrate was concentrated under reduced pressure. The residue was purified by silica gel column chromatography to give Compound (a)-9 (0.928 g, 95%).

¹H-NMR (CDCl₃) δ: 7.99 (1H, d, J=2.4 Hz), 7.38 (1H, dd, J=8.8, 2.4 Hz), 6.53 (1H, d, J=8.8 Hz), 4.50 (2H, brs), 4.24 (2H, s), 3.78 (2H, t, J=5.1 Hz), 3.67 (2H, t, J=5.4 Hz), 1.50 (9H, s)

<Synthesis of Compound (a)-10>

Compound (a)-10, tert-butyl (R)-4-(6-((6-(1-(benzoyloxy) ethyl)-8-(isopropylamino)pyrido[3,4-d]pyrimidin-2-yl)amino)pyridin-3-yl)-3-oxopiperazine-1-carboxylate, was synthesized.

[Chemical formula 12]

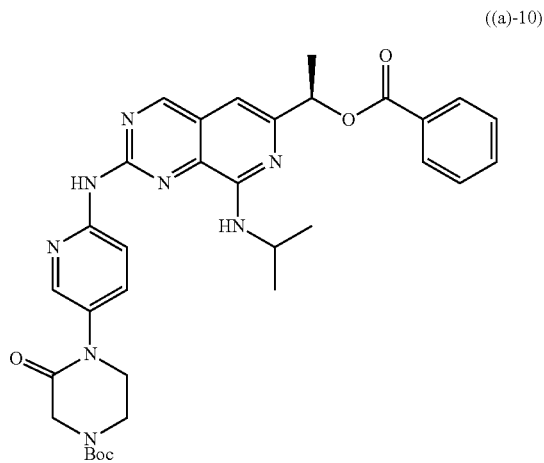

((a)-10)

Compound (a)-7 (62 mg, 0.15 mmol) and Compound (a)-9 (88 mg, 0.30 mmol) were stirred in toluene (0.375 ml) at 100° C. for six days. The solution was purified by silica gel column chromatography to give titled Compound (a)-10 (0.0092 g, 10%).

$^1$H-NMR (DMSO) δ: 10.27 (1H, s), 9.27 (1H, s), 8.33 (2H, m), 8.07 (2H, m), 7.86 (1H, m), 7.70 (1H, m), 7.58 (3H, m), 7.00 (1H, s), 6.55 (1H, d), 5.98 (1H, q), 4.27 (1H, m), 4.11 (2H, s), 3.74 (4H, m), 1.68 (3H, d), 1.45 (9H, s), 1.30 (6H, m)

<Synthesis and Purification of Compound (a)>

Compound (a), 1-(6-((6-((1R)-1-hydroxyethyl)-8-(isopropylamino)pyrido[3,4-d]pyrimidin-2-yl)amino)-3-pyridyl)piperazin-2-one, was synthesized.

[Chemical formula 13]

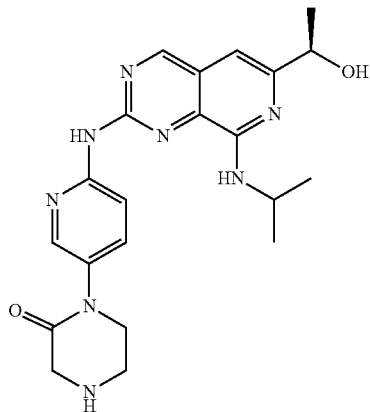

(a)

Trifluoroacetic acid (0.15 ml) was added to a solution of Compound (a)-10 (9.2 mg, 0.15 mmol) in dichloromethane (0.35 ml) at room temperature, and the solution was stirred for one hour. After the solution was evaporated to dryness, tetrahydrofuran (0.15 ml) and methanol (0.15 ml) was added, and then aqueous 4M lithium hydroxide solution (0.018 ml) was added. The solution after the reaction was neutralized with formic acid, the resultant was purified by silica gel column chromatography to give a titled compound.

$^1$H-NMR (DMSO) δ: 10.16 (1H, s), 9.26 (1H, s), 8.31 (1H, m), 8.29 (1H, s), 7.81 (1H, m), 7.00 (1H, s), 6.42 (1H, m), 5.18 (1H, d), 4.63 (1H, m), 4.27 (1H, m), 3.65 (2H, m), 3.41 (2H, s), 3.05 (2H, m), 1.39 (3H, d), 1.30 (6H, m)

<Production of Crystal D of Compound (a)>

The solution of Compound (a) purified by the silica gel column chromatography was concentrated until crystals were precipitated. Crystal D of Compound (a) was thereby prepared.

<Evaluation of Crystal D of Compound (a)>

FIG. 1 illustrates the X-ray diffraction spectrum of the resulting crystal. Peaks were observed at 6.3°, 6.6°, 11.6°, 16.9°, and 20.0° (diffraction angle 2θ).

The heat flow curve by differential scanning calorimetry (DSC) had an endothermic peak at 277° C.

FIG. 10 illustrates the IR absorption spectrum (KBr) of the crystal. Absorption Peaks were observed at 703 $cm^{-1}$, 896 $cm^{-1}$ and 3418 $cm^{-1}$ (wave number).

FIGS. 17-1 and 17-2 illustrate solid $^{13}$C-NMR spectra of the crystal. FIG. 17-1 exhibits 6500 Hz mode and FIG. 17-2 exhibits 14000 Hz mode. Peaks were observed at 136.0 ppm, 111.2 ppm, 105.1 ppm, 101.8 ppm, 52.7 ppm, 49.6 ppm, 42.9 ppm, 23.8 ppm and 18.5 ppm (chemical shift).

FIG. 18 illustrates the solid $^{15}$N-NMR spectrum of the crystals. Peaks were observed at 248.6 ppm, 245.7 ppm, 229.2 ppm, 214.5 ppm, 174.3 ppm, 86.5 ppm, 54.7 ppm and −12.4 ppm (chemical shift).

Example 2

Example 2 explains Crystal A of 1-(6-((6-((1R)-1-hydroxyethyl)-8-(isopropylamino)pyrido[3,4-d]pyrimidin-2-yl)amino)-3-pyridyl)piperazin-2-one (Compound (a)).

<Production of Crystal a of Compound (a)>

Crystal A of Compound (a) was produced by transformation of Crystal D of Compound (a) prepared in Example 1.

Crystal D was suspended in 5- to 50-fold ethanol. The suspension was heated with stirring for six hours, and then was stirred at 0° C. The precipitant was collected by filtration and dried into crystals.

Although there is no limit on the volume of the solvent, the heating time, the condition of stirring, the time of filtration, these parameters may affect the yield of crystals, chemical purity, particle diameter, and particle size distribution. It is preferred that these parameters be appropriately determined. The crystals can be collected by any common process, for example, spontaneous filtration, pressurized filtration, suction filtration, drying by heating, or drying by heating under reduced pressure.

<Evaluation of Crystal A of Compound (a)>

FIG. 2 illustrates the X-ray diffraction spectrum of the resulting crystal. Peaks were observed at 5.3°, 7.3°, 10.3°, 15.1°, and 17.4° (diffraction angle 2θ).

The heat flow curve by differential scanning calorimetry (DSC) had an endothermic peak at 277° C.

FIG. 11 illustrates the IR absorption spectrum (KBr) of the crystal. Absorption Peaks were observed at 874 $cm^{-1}$, 1330 $cm^{-1}$ and 3314 $cm^{-1}$ (wave number).

FIGS. 19-1 and 19-2 illustrate solid $^{13}$C-NMR spectra of the crystal. FIG. 19-1 exhibits 6500 Hz mode and FIG. 19-2 exhibits 14000 Hz mode. Peaks were observed at 154.7 ppm, 138.8 ppm, 133.6 ppm, 113.2 pm, 101.6 ppm, 100.4 ppm, 67.4 ppm, 51.8 ppm, 26.6 ppm and 23.3 ppm (chemical shift).

FIG. 20 illustrates the solid $^{15}$N-NMR spectrum of the crystals. Peaks were observed at 243.6 ppm, 86.7 ppm, 56.7 ppm and −12.4 ppm (chemical shift).

Example 3

Example 3 explains Crystal B of 1-(6-((6-(((1R)-1-hydroxyethyl)-8-(isopropylamino)pyrido[3,4-d]pyrimidin-2-yl)amino)-3-pyridyl)piperazin-2-one (Compound (a)).

<Production of Crystal B of Compound (a)>

Compound (a) was purified as in Example 1 except that the solvent used in the column chromatography was dichloromethane/methanol=20/1, and the solution of Compound (a) was concentrated until crystals were precipitated. Crystal B of Compound (a) was thereby prepared.

FIG. 6 illustrates the X-ray diffraction spectrum of the resulting crystal. Peaks were observed at 5.3°, 6.0°, 6.7°, 10.4° and 20.8° (diffraction angle 2θ).

The heat flow curve by differential scanning calorimetry (DSC) had an endothermic peak at 271° C.

Example 4

<Production of Crystal C of Compound (a)>

Dimethyl sulfoxide (5.4 mL) was added to Crystal D (900 mg) of Compound (a) and the mixture was heated to 70° C. The resulting solution was cooled to 40° C. Acetonitrile (6.75 mL) was added, cooled to 15° C., then was stirred for two hours. The solid component was collected by filtration, was washed with acetonitrile (2.5 mL), and was dried under reduced pressure at 40° C. to give the adduct of the titled compound (986 mg, 92%) with dimethyl sulfoxide.

<Evaluation of Crystal C of Compound (a)>

FIG. 7 illustrates the X-ray diffraction spectrum of the resulting crystal. Peaks were observed at =6.0°, 10.0°, 13.7°, 20.3° and 23.0° (diffraction angle 2θ).

The heat flow curve by differential scanning calorimetry (DSC) had an endothermic peak at 100° C. and 278° C.

FIG. 12 illustrates the IR absorption spectrum (KBr) of the crystal. Absorption Peaks were observed at 840 cm$^{-1}$, 904 cm$^{-1}$, 955 cm$^{-1}$, 1490 cm$^{-1}$ and 3281 cm$^{-1}$ (wave number).

Example 5

<Production of Crystal I of Compound (a)>

Water (10 mL) was added to Crystal A (500 mg) of Compound (a), the mixture was stirred for four days at room temperature. The resulting solid was collected by filtration, and was dried at 30° C. under reduced pressure to give a titled compound (432 mg, 86%).

<Evaluation of Crystal I of Compound (a)>

FIG. 8 illustrates the X-ray diffraction spectrum of the resulting crystal. Peaks were observed at 5.2°, 7.2°, 9.5°, 14.5°, 16.5°, 20.9°, 25.0° and 27.9° (diffraction angle 2θ).

The heat flow curve by differential scanning calorimetry (DSC) had an endothermic peak at 272° C.

FIG. 13 illustrates the IR absorption spectrum (KBr) of the crystal. Absorption Peaks were observed at 1081 cm$^{-1}$ and 1260 cm$^{-1}$ (wave number).

Example 6

Example 6 explains Crystal A of 1-(6-(((6-(((1R)-1-methoxyethyl)-8-(isopropylamino)pyrido[3,4-d]pyrimidin-2-yl)amino)-3-pyridazyl)piperazin-1-yl(piperazine) (Compound (b)).

Synthesis of Compound (b) will now be described.

<Synthesis of Compound (b)-1>

Compound (b)-1, (R)—N-isopropyl-6-(I-methoxyethyl)-2-(methylthio)pyrido[3,4-d]pyrimidin-8-amine was synthesized.

[Chemical formula 14]

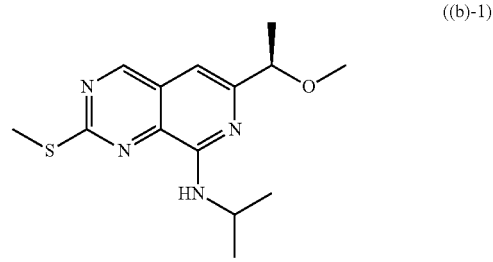

(b)-1

Compound (b)-1 was synthesized as in Compounds (a)-3, (a)-4, (a)-5, and (a)-6.

$^1$H-NMR (DMSO-d$_6$) δ: 9.27 (7H, s), 6.94 (1H, brs), 6.92 (1H, s), 4.30-4.23 (1H, m), 3.29 (3H, s), 2.66 (3H, s), 1.38 (3H, d, J=6.4 Hz), 1.32-1.25 (6H, m)

<Synthesis of Compound (b)-2>

Compound (b)-2, (R)—N-isopropyl-6-(1-methoxyethyl)-2-(methylsulfonyl)pyrido[3,4-d]pyrimidin-8-amine, was synthesized.

[Chemical formula 15]

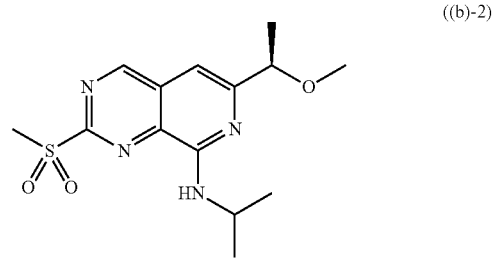

(b)-2

Oxone was added to a solution of Compound (b)-1 in a mixture of tetrahydrofuran (THF) and water at 0° C. and was stirred for 18 hours. The reaction product was extracted with ethyl acetate. The organic layer was washed with water and dried over sodium sulfate, anhydride. After the solvent was removed, the crude product was purified by silica gel column chromatography to give titled Compound (b)-2.

LC/MS: (M+H)$^+$=325.10

<Synthesis of Compound (b)-3>

Compound (b)-3, tert-butyl 4-(6-chloropyridazin-3-yl)piperazine-1-carboxylate, was synthesized.

[Chemical formula 16]

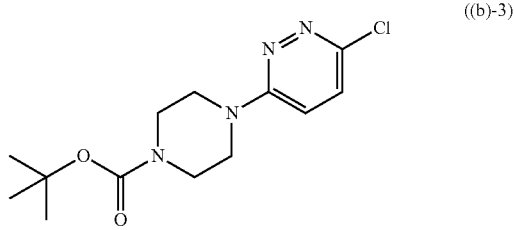

((b)-3)

3,6-Dichloropyridazine (5.01 g, 33.6 mmol) and tert-butylpiperazine carboxylate (6.88 g, 37.0 mmol) was dissolved in DMF (50 mL). Triethylamine (11.7 mL, 50.4 mmol) was added and the mixture was stirred at 80° C. overnight. The solution was cooled to room temperature, and water was added. The product was extracted with a mixed solvent (50 mL) of dichloromethane and methanol (95:5) three times. The combined organic phase was dried over magnesium sulfite, anhydride, and the solid component was collected by filtration. The filtrate was concentrated under reduce pressure. The crude product was washed with diethyl ether to give titled Compound (b)-3 (7.0 g, 70%).

<Synthesis of Compound (b)-4>

Compound (b)-4, tert-butyl 4-(6-((diphenylmethylene)amino)pyridazin-3-yl)piperazine-1-carboxylate, was synthesized.

[Chemical formula 17]

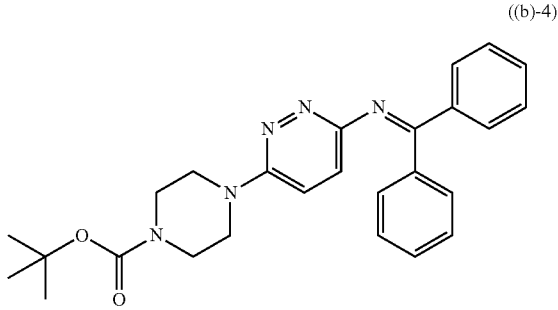

((b)-4)

Compound (b)-3 (59.8 mg, 0.20 mmol), benzophenone imine (43.5 mg, 0.24 mmol), tris(dibenzylideneacetone)dipalladium (9.2 mg, 0.010 mmol), BINAP (2,2'-bis(diphenylphosphino)-1,1'-binaphthyl) (12.5 mg, 0.020 mmol), and cesium carbonate (130.3 mg, 0.40 mmol) were suspended in toluene (1.0 mL), and the suspension was stirred at 100° C. overnight. After the suspension was cooled to room temperature, the solution was filtrated through a Celite pad and the Celite pad was washed with ethyl acetate. The resulting filtrate was washed with saturated brine and dried over magnesium sulfate, anhydride. After the solid component was filtered out, the filtrate was concentrated under reduced pressure. The residue was purified by silica gel column chromatography to give titled Compound (b)-4 (67 mg, 76%).

<Synthesis of Compound (b)-5>

Compound (b)-5, tert-butyl 4-(6-aminopyridazin-3-yl)piperazine-1-carboxylate, was synthesized.

[Chemical formula 18]

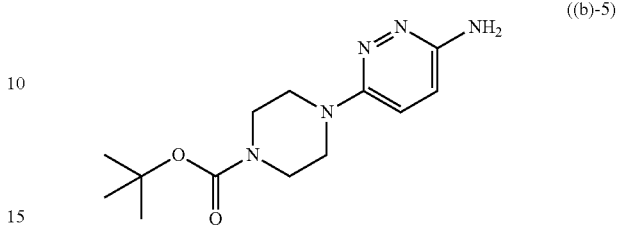

((b)-5)

Compound (b)-4 (67 mg, 0.151 mmol) was dissolved in THF (0.76 mL), and aqueous citric acid solution (0.378 mL, 0.755 mmol, 2 mol/L) was added. The solution was stirred at room temperature overnight. The reaction system was neutralized with aqueous saturated sodium hydrogen carbonate solution (5 mL), and the product was extracted with ethyl acetate (5 mL) two times. The organic phases were combined and dried over magnesium sulfate, anhydride. After the solid components were filtered out, the filtrate was concentrated under reduced pressure. The crude product was washed with tert-butyl methyl ether (5 mL) to give titled Compound (b)-5 (0.30 g, 71%).

Synthesis of compounds related to the inventive examples, i.e., 6-aminopyridine-3-carbaldehyde and tert-butyl 4-[(6-aminopyridin-3-yl)methyl]piperazine-1-carboxylate will now be described in the following Reference Examples.

<Synthesis of Compound (b)-6>

Compound (b)-6, tert-butyl (R)-4-(6-((8-(isopropylamino)-6-(1-methoxyethyl)pyrido[3,4-d]pyrimidin-2-yl)amino)pyridazin-3-yl)piperazine-1-carboxylate, was synthesized.

[Chemical formula 19]

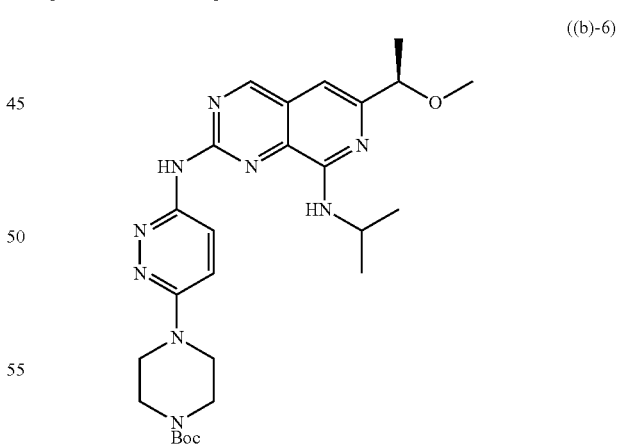

((b)-6)

A solution of Compound (a)-5 (708 mg, 2.2 mmol) and Compound (b)-5 (732 mg, 2.6 mmol) synthesized in Example 1 in toluene (5.5 ml) was stirred for three days at 100° C. After being cooled to room temperature, the solution was diluted with ethyl acetate (20 ml) and dichloromethane (100 ml). The solution was washed with saturated brine (90 ml) then saturated aqueous sodium hydrogen carbonate solution (10 ml). The isolated organic phase was evaporated to dryness, was purified through a silica gel column to give titled Compound (b)-6 (510 mg, 45%).

<Synthesis of Compound (b)>

Compound (b), 1-(6-((6-((1R)-1-methoxyethyl)-8-(isopropylamino)pyrido[3,4-d]pyrimidin-2-yl)amino)-3-pyridazyl)piperazin-1-yl(piperazine), was synthesized.

[Chemical formula 20]

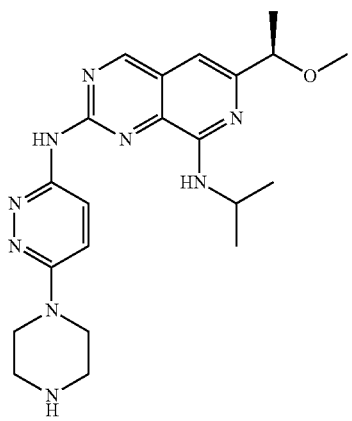

(b)

Trifluoroacetic acid (0.2 ml) was added to a solution of Compound (b)-6 (33.2 mg, 0.063 mmol) in dichloromethane (0.44 ml) at room temperature, and the mixture was stirred for one hour at room temperature. The solution was concentrated into dryness, and the product was purified by preparative HPLC to give titled Compound (23.8 mg, 88%).

$^1$H-NMR (DMSO) δ: 10.24 (1H, s), 9.20 (1H, s), 8.16 (1H, d), 7.36 (1H, d), 6.86 (1H, s), 6.35 (1H, d), 6.42 (1H, m), 4.22 (2H, m), 3.43 (4H, m), 3.26 (4H, m), 2.81 (3H, m), 1.37 (3H, d), 1.26 (6H, m)

<Production of Crystal A of Compound (b)>

Trifluoroacetic acid (TFA) salt of Compound (b) purified by preparative HPLC was prepared. The TFA salt was agitated in a mixture of water and dichloromethane. The pH of the aqueous phase was adjusted to be weak alkaline (pH 8 to 9) with saturated aqueous sodium hydrogen carbonate solution, and the organic phase was isolated. After the organic phase was washed with saturated brine and dried over sodium sulfate, anhydride, the solvent was removed to give Crystal A.

<Evaluation of Crystal A of Compound (b)>

FIG. 3 illustrates the X-ray diffraction spectrum of the resulting crystal. Peaks were observed at 5.2°, 7.6°, 8.4°, 10.5°, 15.2°, 16.9°, 20.1°, 21.0°, 23.3° and 26.6° (diffraction angle 2θ).

The heat flow curve by differential scanning calorimetry (DSC) had an endothermic peak at 225° C.

FIG. 14 illustrates the IR absorption spectrum (KBr) of the crystal. Absorption Peaks were observed at 1369 cm$^{-1}$, 1424 cm$^{-1}$, 1508 cm$^{-1}$, 1545 cm$^{-1}$ and 1566 cm$^{-1}$ (wave number).

FIGS. 21-1 and 21-2 illustrate solid $^{13}$C-NMR spectra of the crystal. FIG. 21-1 exhibits 6500 Hz mode and FIG. 21-2 exhibits 14000 Hz mode. Peaks were observed at 163.4 ppm, 157.6 ppm, 155.5 ppm, 117.8 ppm, 82.2 ppm, 56.1 ppm and 42.3 ppm (chemical shift).

FIG. 22 illustrates the solid $^{15}$N-NMR spectrum of the crystals. Peaks were observed at 311.7 ppm, 232.4 ppm, 168.5 ppm, 79.5 ppm, 53.3 ppm, 32.9 ppm and −4.3 ppm (chemical shift).

Examples 7

Example 7 explains Crystal B of 1-(6-((6-((1R)-1-methoxyethyl)-8-(isopropylamino)pyrido[3,4-d]pyrimidin-2-yl)amino)-3-pyridazyl)piperazin-1-yl(piperazine) (Compound (b)).

<Production of Crystal B of Compound (b)>

Tetrahydrofuran (0.15 ml) and methanol (0.15 ml) were added to the TFA salt precipitated during the production of Crystal A, and then aqueous 4M lithium hydroxide solution (0.018 ml) was added. The solution was neutralized with formic acid, and the product was purified by silica gel column chromatography. The solution of Compound (b) was concentrated until crystals were precipitated. Crystal B of Compound (b) was thereby prepared.

<Evaluation of Crystal B of Compound (b)>

FIG. 4 illustrates the X-ray diffraction spectrum of the resulting crystal. Peaks were observed at 5.2°, 6.6°, 8.1°, 15.2°, 15.9°, 16.2°, 18.8°, 20.5°, 20.8°, and 21.7° (diffraction angle 2θ).

The heat flow curve by differential scanning calorimetry (DSC) had an endothermic peak at 221° C.

Example 8

<Production of Crystal C of Compound (b)>

Ethanol (11 mL) was added to Crystal C (1.1 g) of Compound (b), and the mixture was stirred overnight at room temperature. The resulting solid component was collected by filtration and dried at 40° C. under reduced pressure to give a titled compound (945 mg, 86%).

<Evaluation of Crystal C of Compound (b)>

FIG. 9 illustrates the X-ray diffraction spectrum of the resulting crystal. Peaks were observed at =5.2°, 7.6°, 8.4°, 10.0°, 10.5°, 11.9°, 15.2°, 17.0°, 20.9° and 21.2° (diffraction angle 2θ).

The heat flow curve by differential scanning calorimetry (DSC) had an endothermic peak at 223° C.

FIG. 15 illustrates the IR absorption spectrum (KBr) of the crystal. Absorption Peaks were observed at 1369 cm$^{-1}$, 1424 cm$^{-1}$, 1507 cm$^{-1}$, 1546 cm$^{-1}$ and 1566 cm$^{-1}$ (wave number).

Example 9

Example 9 explains Crystal A of (R)—N8-isopropyl-6-(1-methoxyethyl)-N2-(5-(piperazan-1-ylmethyl)pyridin-2-yl)pyrido[3,4-d]pyrimidin-2,8-diamine (Compound (c)).

Synthesis of Compound (c) will now be described.

<Synthesis of Compound (c)-1>

Compound (c)-1, 6-aminopyridine-3-carbaldehyde was synthesized.

[Chemical formula 21]

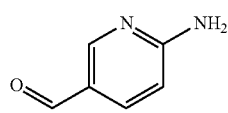

((c)-1)

6-Aminopyridine-3-carbonitrile (1.9 g, 16 mmol) was dissolved in THF (160 mL), and the solution was cooled with stirring to −78° C. Diisobutylaluminum hydride (106.5 mL, 1.5M toluene solution) was gradually added dropwise to the solution at −78° C., heated with stirring to 20° C., and further stirred for two hours. Iced water (100 mL) was added to the solution to quench the reaction. The product was extracted with dichloromethane (50 mL) three times. After the resulting organic phases were combined, the solution was washed with brine (100 mL) one time and dried over sodium sulfate, anhydride. After the solid component was filtered out, the filtrate was concentrated under reduced pressure. The residue was purified by silica gel chromatography to give crude titled Compound (c)-1 (1.7 g). The crude product was used in the following reaction without further purification.

<Synthesis of Compound (c)-2>

Compound (c)-2, tert-butyl 4-[(6-amino pyridin-3-yl) methyl]piperazine-1-carboxylate was synthesized.

[Chemical formula 22]

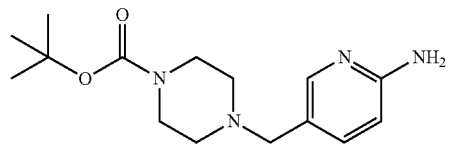

((c)-2)

6-Aminopyridine-3-carbonitrile (1.9 g, 16 mmol) was dissolved in THF (160 mL), and the mixture was cooled with stirring to −78° C. Diisobutylaluminum hydride (106.5 mL, 1.5 M toluene solution) was gradually added dropwise to the solution at −78° C. The system was heated with stirring to 20° C., and further stirred for two hours. Iced water (100 mL) was added to the solution to quench the reaction. The product was extracted with dichloromethane (50 mL) three times. After the organic phases were combined, the solution was washed with brine (100 mL) one time and dried over sodium sulfate, anhydride. After the solid component was filtered out, the filtrate was concentrated under reduced pressure. The residue was purified by silica gel chromatography to give a crude titled compound (1.7 g).

The resulting crude product (1.7 g, 13.9 mmol) and tert-butyl piperazine-1-carboxylate (3.2 g, 17.2 mmol) were dissolved in dichloromethane (50 mL), and the mixture was stirred for eight hours at room temperature. Sodium triacetoxyborohydride (8.84 g, 40.9 mmol) was added to the solution and the mixture was stirred for two hours at room temperature. The reaction was traced by LC/MS. After the completion of the reaction, saturated aqueous sodium carbonate solution (50 mL) was added to quench the reaction. The product was extracted with ethyl acetate (50 mL) three times. After the resulting organic phases were combined, the solution was washed with brine (100 mL) one time and dried over sodium sulfate, anhydride. After the solid component was filtered out, the filtrate was concentrated under reduced pressure. The residue was purified by silica gel chromatography to give a crude titled compound (3.8 g, 81%).

<Synthesis of Compound (c)-3>

Compound (c)-3, tert-butyl (R)-4-((6-((8-(isopropylamino)-6-(1-methoxyethyl)pyrido[3,4-d]pyrimidin-2-yl) amino) pyridin-3-yl)methyl)piperazine-1-carboxylate, was synthesized.

[Chemical formula 23]

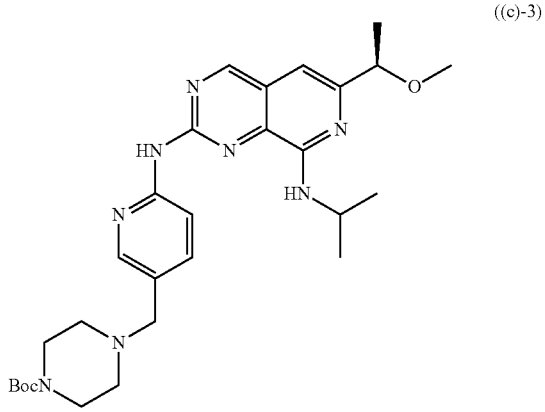

((c)-3)

Titled Compound (c)-3 was synthesized as in Compound (b)-6 using Compounds B-2 and C-2.

<Synthesis of Compound (c)>

Synthesis of Compound (c), (R)—N8-isopropyl-6-(1-methoxyethyl)-N2-(5-(piperazin-1-ylmethyl)pyridin-2-yl) pyrido[3,4-d]pyrimidin-2,8-diamine

[Chemical formula 24]

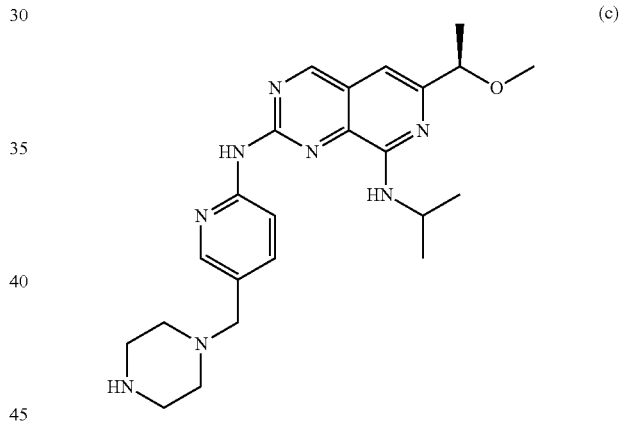

(c)

The titled compound was prepared with Compound (c)-3 as in Compound (a) in Example 1.

$^1$H-NMR (CDCl$_3$) δ: 9.04 (1H, s), 8.34 (1H, d), 8.26 (1H, s), 7.74 (1H, dd), 6.84 (1H, s), 6.14 (1H, d), 4.41 (1H, m), 4.33 (1H, q), 3.49 (2H, s), 3.41 (3H, s), 2.91 (4H, m), 2.46 (4H, br), 1.50 (3H, d), 1.36 (6H, m)

<Production of Crystal A of Compound (c)>

The solution of Compound (c) purified by preparative HPLC was concentrated until crystals were precipitated. Crystal A of Compound (c) was thereby prepared.

<Evaluation of Crystal A of Compound (c)>

FIG. 5 illustrates the X-ray diffraction spectrum of the resulting crystal. Peaks were observed at 4.8°, 7.6°, 8.2°, 9.7°, 15.3°, 16.6°, 19.1°, 19.8°, 22.4° and 26.2° (diffraction angle 2θ).

The heat flow curve by differential scanning calorimetry (DSC) had an endothermic peak at 182° C.

FIG. 16 illustrates the IR absorption spectrum (KBr) of the crystal. Absorption Peaks were observed at 1115 cm$^{-1}$, 1446 cm$^{-1}$, 1508 cm$^{-1}$, 1560 cm$^{-1}$ and 1601 cm$^{-1}$ (wave number).

FIGS. 23-1 and 23-2 illustrate solid $^{13}$C-NMR spectra of the crystal. FIG. 23-1 exhibits 6500 Hz mode and FIG. 23-2 exhibits 14000 Hz mode. Peaks were observed at 161.3 ppm, 150.8 ppm, 138.9 ppm, 128.1 ppm, 109.8 ppm, 82.7 ppm, 47.6 ppm, 42.5 ppm, 41.5 ppm, 24.5 ppm and 21.7 ppm (chemical shift).

FIG. 24 illustrates the solid $^{15}$N-NMR spectrum of the crystals. Peaks were observed at 242.8 ppm, 233.8 ppm, 219.0 ppm, 171.7 ppm, 86.9 ppm, 54.9 ppm, 11.3 ppm and −5.5 ppm (chemical shift).

Example 10

Evaluation of Inhibitory Activity Against Human CDK4/Cyclin D3

The inhibitory activities against human CDK4/cyclin D3 of Compounds (a), (b), and (c) were evaluated.

The inhibitory activity against human CDK4/cyclin D3 of each compound was determined with an assay kit (QS S Assist CDK4/Cyclin D3_FP kit) available from Carna Biosciences, Inc. This assay kit can determine the kinase activity involving determination of a variation in fluorescence polarization caused by binding of a fluorescent substrate phosphorylated by kinase to an IMAP binding reagent based on the IMAP technology by Molecular Devices.

An assay buffer (10×) contained in the kit or a laboratory-made assay buffer having the same composition as that of the kit were used for preparation of sample solutions. The assay buffer (10×) contained in the kit was diluted with purified water to ten folds to prepare an assay buffer. The assay buffer contained 20 mM HEPES (pH 7.4), 0.01% Tween 20, and 2 mM dithiothreitol. The test compound was prepared with dimethyl sulfoxide (DMSO) into a concentration 100 times the final concentration, and then diluted with the assay buffer to 25 folds, so that the concentration of the test compound solution was four times the final concentration. The ATP (5×)/substrate/Metal solution contained in the kit was diluted with the assay buffer to five folds before use. The CDK4/cyclin D3 contained in the kit was diluted with the assay buffer into a concentration two times the final concentration to prepare an enzyme solution (the final concentration of the CDK4/cyclin D3 was 12.5 to 25 ng/well). The IMAP (5×) binding buffer A and IMAP (5×) binding buffer B were each diluted with purified water to five folds, these buffers were mixed such that the ratio of the IMAP binding buffer A to the IMAP binding buffer B was 85:15, and the IMAP binding reagent was added so as to be 400-fold dilution to prepare a detection reagent.

The test compound solution (5 µL) and the ATP/substrate/Metal solution (5 µL) were placed on to a 384-well plate. After the enzyme solution or assay buffer (10 µL) was placed, the solution was mixed to start the enzyme reaction. The total volume of the solution was 20 µL/well, and the reaction solution contained 20 mM HEPES (pH7.4), 0.01% Tween 20, 2 mM dithiothreitol, 100 nM FITC-labeled peptide substrate (Carna Biosciences, Inc.), 100 µM ATP, 1 mM magnesium chloride, 1% DMSO, and 12.5 to 25 ng/well CDK4/cyclin D3. After the reaction for 45 minutes at room temperature, the detection reagent (60 µL) was added to each well, the reaction was further continued for 30 minutes at room temperature under a light shielding condition. The fluorescence polarization was measured at an excitation wavelength of 485 nm and a detection wavelength of 535 nm with a microplate reader.

The enzyme solution was added and the percent inhibition of the enzyme activity of the test compound was determined where the enzyme activity when DMSO was added in place of the test compound solution was defined as 100% and the enzyme activity when the assay buffer was added in place of the enzyme solution and DMSO was added in place of the test compound solution was defined as 0%. The percent inhibition was fit on a dose-response curve to calculate the 50% inhibitory concentration against the CDK4/cyclin D3.

The inhibitory activity $IC_{50}$ of each compound against the CDK4/cyclin D3 activity was less than 10 nM.

Example 11

Evaluation of Inhibitory Activity of Human CDK2/Cyclin A2

Compounds A, B, and C were subjected to evaluation of inhibitory activity against human CDK2/cyclin A2 using an assay kit (QS S Assist CDK2/Cyclin A2_FP kit) available from Carna Biosciences, Inc. This assay kit can determine the kinase activity involving determination of a variation in fluorescence polarization caused by binding of a fluorescent substrate phosphorylated by kinase to an IMAP binding reagent based on the IMAP technology by Molecular Devices.

The assay buffer (10×) contained in the kit was diluted with purified water to ten folds to prepare an assay buffer, which was then used for preparation of each solution. The assay buffer contained 20 mM HEPES (pH 7.4), 0.01% Tween 20, and 2 mM dithiothreitol. Each test compound was diluted with dimethyl sulfoxide (DMSO) into a concentration 100 times the final concentration and then diluted with the assay buffer to 25 folds, so that the concentration of the test compound was four times the final concentration, to prepare a test compound solution. The ATP (5×/substrate/Metal solution contained in the kit was diluted with the assay buffer to five folds before use. The CDK2/cyclin A2 contained in the kit was diluted with the assay buffer into a concentration two times the final concentration to prepare an enzyme solution (the final concentration of the CDK2/cyclin A2 was 2.5 ng/well). The IMAP (5×) binding buffer A was diluted with purified water to five folds and the IMAP binding reagent was added into 400 fold dilution to prepare a detection reagent.

The test compound solution (5 µL) and the ATP/substrate/Metal solution (5 µL) were placed on to a 384-well plate. After the enzyme solution or assay buffer (10 µL) was placed, the solution was mixed to start the enzyme reaction. The total volume of the solution was 20 µL/well, and the reaction solution contained 20 mM HEPES (pH7.4), 0.01% Tween 20, 2 mM dithiothreitol, 100 nM FITC-labeled peptide substrate (Carna Biosciences, Inc.), 30 µM ATP, 5 mM magnesium chloride, 1% DMSO, and 2.5 ng/well CDK2/cyclin A2. After the reaction for 60 minutes at room temperature, the detection reagent (60 µL) was added to each well, the reaction was further continued for 30 minutes at room temperature under a light shielding condition. The fluorescence polarization was measured at an excitation wavelength of 485 nm and a detection wavelength of 535 nm with a microplate reader.

The enzyme solution was added and the percent inhibition of the enzyme activity of the test compound was determined where the enzyme activity when DMSO was added in place of the test compound solution was defined as 100% and the enzyme activity when the assay buffer was added in place of the enzyme solution and DMSO was added in place of the test compound solution was defined as 0%. The percent inhibition was fit on a dose-response curve to calculate the 50% inhibitory concentration against the CDK2/cyclin A2.

The inhibitory activity $IC_{50}$ of each compound against the CDK4/cyclin D3 activity was equal or less than 100 nM.

Example 12

Evaluation of Inhibitory Activity Against Human CDK6/Cyclin D3

The inhibitory activity of CDK6/cyclin D3 was determined by Off-chip Mobility Shift Assay (MSA). The MSA can determine the kinase activity involving separation of proteins by means of a difference in mobility during electrophoresis depending on the molecular weight and electrical charge of each protein. The kinase activity was determined through electrophoretic separation of proteins having different electronegativities depending on the proportion of the phosphorylation by the kinase.

Each solution was prepared with an assay buffer containing 20 mM HEPES (pH 7.5), 0.01% Triton X-100, and 2 mM dithiothreitol. Each test compound was diluted with dimethyl sulfoxide (DMSO) into a concentration 100 times the final concentration and then diluted with the assay buffer to 25 folds, so that the concentration of the test compound was four times the final concentration, to prepare a test compound solution. The ATP/substrate/Metal solution was prepared such that the concentration was four times the final concentration. The enzyme solution was prepared such that the concentration was two times the final concentration. The final concentration of the enzyme was appropriately adjusted based on the signal by the enzyme activity and the inhibitory activity of the positive control compound.

The test compound solution (5 µL) and the ATP/substrate/Metal solution (5 µL) were placed on to a 384-well plate. After the enzyme solution or assay buffer (10 µL) was placed, the solution was mixed to start the enzyme reaction. The total volume of the solution was 20 µL/well, and the reaction solution contained 20 mM HEPES (pH7.5), 0.01% Triton X-100, 2 mM dithiothreitol, 1000 nM peptide substrate (DYRKtide-F), 300 µM ATP, 5 mM magnesium chloride, 1% DMSO, and CDK6/cyclin D3 with a designed concentration. After the reaction for five hours at room temperature, a termination buffer (QuickScout Screening Assist MSA; Carna Biosciences, Inc.) (60 µL) was added to each well to quench the reaction. The substrate peptide and phosphorylated peptide in the solution were separated and determined with LabChip 3000 (Caliper Lifesciences). The kinase reactivity was evaluated by the product ratio (P/(P+S) of the peak height (S) of the substrate peptide to the peak height (P) of the phosphorylated peptide.

The enzyme solution was added and the percent inhibition of the enzyme activity of the test compound was determined where the enzyme activity when DMSO was added in place of the test compound solution was defined as 100% and the enzyme activity when the assay buffer was added in place of the enzyme solution and DMSO was added in place of the test compound solution was defined as 0%. The percent inhibition was fit on a dose-response curve to calculate the 50% inhibitory concentration against the CDK6/cyclin D3.

The inhibitory activity $IC_{50}$ of each compound against the CDK6/cyclin D3 activity was less than 10 nM.

INDUSTRIAL APPLICABILITY

The crystal of the compound of formula (I) according to the present invention can be used as an active ingredient for manufacturing a pharmaceutical.

The invention claimed is:

1. A crystal, wherein said crystal is a crystal of a compound or a crystal of a solvate of said compound, wherein said compound is 1-(6-((6-((1R)-1-hydroxyethyl)-8-(isopropylamino)pyrido[3,4-d]pyrimidin-2-yl)amino)-3-pyridyl)piperazine-2-one, and wherein said crystal is selected from the group consisting of:
   (a) a crystal which exhibits peaks at diffraction angles 2θ=6.3°, 6.6°, 11.6°, 16.9° and 20.0° on a powder X-ray diffraction spectrum;
   (b) a crystal which exhibits peaks at diffraction angles 2θ=5.3°, 7.3°, 10.3°, 15.1° and 17.4° on a powder X-ray diffraction spectrum;
   (c) a crystal which exhibits peaks at diffraction angles 2θ=5.3°, 6.0°, 6.7°, 10.4° and 20.8° on a powder X-ray diffraction spectrum;
   (d) a crystal which exhibits peaks at diffraction angles 2θ=6.0°, 10.0°, 13.7°, 20.3° and 23.0° on a powder X-ray diffraction spectrum; and
   (e) a crystal which exhibits peaks at diffraction angles 2θ=5.2°, 7.2°, 9.5°, 14.5°, 16.5°, 20.9°, 25.0° and 27.9° on a powder X-ray diffraction spectrum.

2. The crystal according to claim 1, which exhibits peaks at diffraction angles 2θ=6.3°, 6.6°, 11.6°, 16.9° and 20.0° on a powder X-ray diffraction spectrum.

3. The crystal according to claim 2, which exhibits an extrapolated onset temperature for an endothermic peak of 277° C. according to differential scanning calorimetry.

4. The crystal according to claim 2, which exhibits distinctive absorption peaks with wave numbers of 703 cm$^{-1}$, 896 cm$^{-1}$ and 3418 cm$^{-1}$ on an infrared absorption spectrum (KBr method).

5. The crystal according to claim 2, which exhibits distinctive peaks at 136.0 ppm, 111.2 ppm, 105.1 ppm, 101.8 ppm, 52.7 ppm, 49.6 ppm, 42.9 ppm, 23.8 ppm and 18.5 ppm on a solid NMR spectrum ($^{13}$C).

6. The crystal according to claim 2, which exhibits distinctive peaks at 248.6 ppm, 245.7 ppm, 229.2 ppm, 214.5 ppm, 174.3 ppm, 86.5 ppm, 54.7 ppm and −12.4 ppm on a solid NMR spectrum ($^{15}$N).

7. The crystal according to claim 1, which exhibits peaks at diffraction angles 2θ=5.3°, 7.3°, 10.3°, 15.1° and 17.4° on a powder X-ray diffraction spectrum.

8. The crystal according to claim 7, which exhibits an extrapolated onset temperature for an endothermic peak of 277° C. according to differential scanning calorimetry.

9. The crystal according to claim 7, which exhibits distinctive absorption peaks with wave numbers of 874 cm$^{-1}$, 1330 cm$^{-1}$ and 3314 cm$^{-1}$ on an infrared absorption spectrum (KBr method).

10. The crystal according to claim 7, which exhibits distinctive peaks at 154.7 ppm, 138.8 ppm, 133.6 ppm, 113.2 ppm, 101.6 ppm, 100.4 ppm, 67.4 ppm, 51.8 ppm, 26.6 ppm and 23.3 ppm on a solid NMR spectrum ($^{13}$C).

11. The crystal according to claim 7, which exhibits distinctive peaks at 243.6 ppm, 86.7 ppm, 56.7 ppm and −12.4 ppm on a solid NMR spectrum ($^{15}$N).

12. The crystal according to claim 1, which exhibits peaks at diffraction angles 2θ=5.3°, 6.0°, 6.7°, 10.4° and 20.8° on a powder X-ray diffraction spectrum.

13. The crystal according to claim 12, which exhibits an extrapolated onset temperature for an endothermic peak of 271° C. according to differential scanning calorimetry.

14. The crystal according to claim 1, which exhibits peaks at diffraction angles 2θ=6.0°, 10.0°, 13.7°, 20.3° and 23.0° on a powder X-ray diffraction spectrum.

15. The crystal according to claim 14, which exhibits an extrapolated onset temperature for an endothermic peak of 100° C. and 278° C. according to differential scanning calorimetry.

16. The crystal according to claim 14, which exhibits distinctive absorption peaks with wave numbers of 840 $cm^{-1}$, 904 $cm^{-1}$, 955 $cm^{-1}$, 1490 $cm^{-1}$ and 3281 $cm^{-1}$ on an infrared absorption spectrum (KBr method).

17. The crystal according to claim 1, which exhibits peaks at diffraction angles 2θ=5.2°, 7.2°, 9.5°, 14.5°, 16.5°, 20.9°, 25.0° and 27.9° on a powder X-ray diffraction spectrum.

18. The crystal according to claim 17, which exhibits an extrapolated onset temperature for an endothermic peak of 272° C. according to differential scanning calorimetry.

19. The crystal according to claim 17, which exhibits distinctive absorption peaks with wave numbers of 1081 $cm^{-1}$ and 1260 $cm^{-1}$ on an infrared absorption spectrum (KBr method).

20. A crystal of a solvate of 1-(6-((6-((1R)-1-methoxyethyl)-8-(isopropylamino)pyrido[3,4-d]pyrimidine-2-yl)amino)-3-pyridazyl)piperazine with dimethyl sulfoxide, wherein said crystal is selected from the group consisting of:
(a) a crystal which exhibits peaks at diffraction angles 2θ=5.2°, 7.6°, 8.4°, 10.5°, 15.2°, 16.9°, 20.1°, 21.0°, 23.3° and 26.6° on a powder X-ray diffraction spectrum;
(b) a crystal which exhibits peaks at diffraction angles 2θ=5.2°, 6.6°, 8.1°, 15.2°, 15.9°, 16.2°, 18.8°, 20.5°, 20.8° and 21.7° on a powder X-ray diffraction spectrum; and
(c) a crystal which exhibits peaks at diffraction angles 2θ=5.2°, 7.6°, 8.4°, 10.0°, 10.5°, 11.9°, 15.2°, 17.0°, 20.9° and 21.2° on a powder X-ray diffraction spectrum.

21. The crystal according to claim 20, which exhibits peaks at diffraction angles 2θ=5.2°, 7.6°, 8.4°, 10.5°, 15.2°, 16.9°, 20.1°, 21.0°, 23.3° and 26.6° on a powder X-ray diffraction spectrum.

22. The crystal according to claim 21, which exhibits an extrapolated onset temperature for an endothermic peak of 225° C. according to differential scanning calorimetry.

23. The crystal according to claim 21, which exhibits distinctive absorption peaks with wave numbers of 1369 $cm^{-1}$, 1424 $cm^{-1}$, 1508 $cm^{-1}$, 1545 $cm^{-1}$ and 1566 $cm^{-1}$ on an infrared absorption spectrum (KBr method).

24. The crystal according to claim 21, which exhibits distinctive peaks at 163.4 ppm, 157.6 ppm, 155.5 ppm, 117.8 ppm, 82.2 ppm, 56.1 ppm and 42.3 ppm on a solid NMR spectrum ($^{13}$C).

25. The crystal according to claim 21, which exhibits distinctive peaks at 311.7 ppm, 232.4 ppm, 168.5 ppm, 79.5 ppm, 53.3 ppm, 32.9 ppm and −4.3 ppm on a solid NMR spectrum ($^{15}$N).

26. The crystal according to claim 20, which exhibits peaks at diffraction angles 2θ=5.2°, 6.6°, 8.1°, 15.2°, 15.9°, 16.2°, 18.8°, 20.5°, 20.8° and 21.7°, on a powder X-ray diffraction spectrum.

27. The crystal according to claim 26, which exhibits an extrapolated onset temperature for an endothermic peak of 221° C. according to differential scanning calorimetry.

28. The crystal according to claim 20, which exhibits peaks at diffraction angles 2θ=5.2°, 7.6°, 8.4°, 10.0°, 10.5°, 11.9°, 15.2°, 17.0°, 20.9° and 21.2°, on a powder X-ray diffraction spectrum.

29. The crystal according to claim 28, which exhibits an extrapolated onset temperature for an endothermic peak of 223° C. according to differential scanning calorimetry.

30. The crystal according to claim 28, which exhibits distinctive absorption peaks with wave numbers of 1369 $cm^{-1}$, 1424 $cm^{-1}$, 1507 $cm^{-1}$, 1546 $cm^{-1}$ and 1566 $cm^{-1}$ on an infrared absorption spectrum (KBr method).

31. A crystal of (R)—N8-isopropyl-6-(1-methoxyethyl)-N2-(5-(piperazine-1-ylmethyl)pyridin-2-yl)pyrido[3,4-d]pyrimidine-2,8-diamine, wherein said crystal is a crystal which exhibits peaks at diffraction angles 2θ=4.8°, 7.6°, 8.2°, 9.7°, 15.3°, 16.6°, 19.1°, 19.8°, 22.4° and 26.2° on a powder X-ray diffraction spectrum.

32. The crystal according to claim 31, which exhibits an extrapolated onset temperature for an endothermic peak of 182° C. according to differential scanning calorimetry.

33. The crystal according to claim 31, which exhibits distinctive absorption peaks with wave numbers of 1115 $cm^{-1}$, 1446 $cm^{-1}$, 1508 $cm^{-1}$, 1560 $cm^{-1}$ and 1601 $cm^{-1}$ on an infrared absorption spectrum (KBr method).

34. The crystal according to claim 31, which exhibits distinctive peaks at 161.3 ppm, 150.8 ppm, 138.9 ppm, 128.1 ppm, 109.8 ppm, 82.7 ppm, 47.6 ppm, 42.5 ppm, 41.5 ppm, 24.5 ppm and 21.7 ppm on a solid NMR spectrum ($^{13}$C).

35. The crystal according to claim 31, which exhibits distinctive peaks at 242.8 ppm, 233.8 ppm, 219.0 ppm, 171.7 ppm, 86.9 ppm, 54.9 ppm, 11.3 ppm and −5.5 ppm on a solid NMR spectrum ($^{15}$N).

36. A pharmaceutical composition comprising a crystal according to claim 1 and a pharmaceutically acceptable carrier.

37. A pharmaceutical composition having a CDK4/6 inhibitory activity, comprising a crystal according to claim 1 as an active ingredient.

38. A pharmaceutical composition comprising a crystal according to claim 20 and a pharmaceutically acceptable carrier.

39. A pharmaceutical composition having a CDK4/6 inhibitory activity, comprising a crystal according to claim 20 as an active ingredient.

40. A pharmaceutical composition comprising a crystal according to claim 31 and a pharmaceutically acceptable carrier.

41. A pharmaceutical composition having a CDK4/6 inhibitory activity, comprising a crystal according to claim 31 as an active ingredient.

* * * * *